United States Patent
Sakurai et al.

(10) Patent No.: US 9,716,189 B2
(45) Date of Patent: Jul. 25, 2017

(54) CYCLIC CARBODIIMIDE COMPOUND, POLYESTER FILM, BACK SHEET FOR SOLAR CELL MODULE, AND SOLAR CELL MODULE

(71) Applicant: FUJIFILM Corporation, Tokyo (JP)

(72) Inventors: Seiya Sakurai, Shizuoka (JP); Makoto Fukuda, Shizuoka (JP)

(73) Assignee: FUJIFILM CORPORATION, Tokyo (JP)

( * ) Notice: Subject to any disclaimer, the term of this patent is extended or adjusted under 35 U.S.C. 154(b) by 47 days.

(21) Appl. No.: 14/539,689

(22) Filed: Nov. 12, 2014

(65) Prior Publication Data

US 2015/0068602 A1  Mar. 12, 2015

Related U.S. Application Data

(63) Continuation of application No. PCT/JP2013/062184, filed on Apr. 25, 2013.

(30) Foreign Application Priority Data

May 17, 2012 (JP) ................. 2012-113227
Aug. 15, 2012 (JP) ................. 2012-180258

(51) Int. Cl.
C07D 273/08 (2006.01)
C07D 498/10 (2006.01)
H01L 31/0203 (2014.01)
B29C 55/12 (2006.01)
C07D 513/10 (2006.01)
C07D 285/00 (2006.01)
C08J 5/18 (2006.01)
H01L 31/049 (2014.01)
C08G 63/91 (2006.01)
C08K 5/29 (2006.01)

(52) U.S. Cl.
CPC .......... *H01L 31/0203* (2013.01); *B29C 55/12* (2013.01); *C07D 273/08* (2013.01); *C07D 285/00* (2013.01); *C07D 498/10* (2013.01); *C07D 513/10* (2013.01); *C08G 63/916* (2013.01); *C08J 5/18* (2013.01); *C08K 5/29* (2013.01); *H01L 31/049* (2014.12); *C08J 2367/02* (2013.01); *Y02E 10/50* (2013.01)

(58) Field of Classification Search
None
See application file for complete search history.

(56) References Cited

U.S. PATENT DOCUMENTS

| | | |
|---|---|---|
| 8,592,529 B2 | 11/2013 | Shoji et al. |
| 8,816,018 B2 | 8/2014 | Shoji et al. |
| 8,987,440 B2 | 3/2015 | Shoji et al. |
| 2011/0224385 A1 | 9/2011 | Shoji et al. |
| 2011/0237755 A1 | 9/2011 | Shoji et al. |
| 2011/0251384 A1 | 10/2011 | Shoji et al. |
| 2012/0302676 A1 | 11/2012 | Oya et al. |
| 2013/0005875 A1 | 1/2013 | Shoji et al. |
| 2013/0079510 A1* | 3/2013 | Shoji ............... C07D 498/10 540/466 |

FOREIGN PATENT DOCUMENTS

| | | |
|---|---|---|
| CN | 102245585 | 11/2011 |
| JP | 2011-258641 A | 12/2011 |
| WO | 2010/071211 A1 | 6/2010 |

OTHER PUBLICATIONS

Second Office Action issued by the State Intellectual Property Office of China on Dec. 28, 2015 in connection with Chinese Patent Application No. 201380025445.9.
International Search Report and Written Opinion issued by the International Bureau of WIPO on Nov. 27, 2014 in connection with Appl. No. PCT/JP2013/062184.
International Search Report issued in PCT/JP2013/062184 on Jul. 30, 2013.
Written Opinion issued in PCT/JP2013/062184 on Jul. 30, 2013.
First Office Action issued by the State Intellectual Property Office of China on May 25, 2015 in connection with Chinese Patent Application No. 201380025445.9.

* cited by examiner

*Primary Examiner* — Noble Jarrell
(74) *Attorney, Agent, or Firm* — Jean C. Edwards, Esq.; Edwards Neils LLC

(57) ABSTRACT

A polyester film including a cyclic carbodiimide compound represented by the following Formula (O-1) has good film thickness uniformity without increase in viscosity. $R^1$ and $R^5$ represent an alkyl group, an aryl group, or an alkoxy group; $R^2$ to $R^4$ and $R^6$ to $R^8$ represent a hydrogen atom, an alkyl group, an aryl group, or an alkoxy group; $X^1$ and $X^2$ represent a single bond, —O—, —CO—, —S—, —SO$_2$—, —NH—, or —CH$_2$—; and $L^1$ represents a divalent linking group.

Formula (O-1)

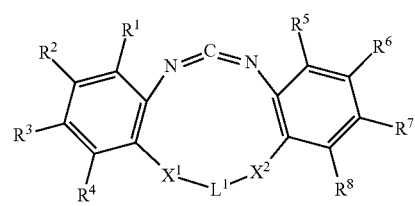

11 Claims, No Drawings

CYCLIC CARBODIIMIDE COMPOUND, POLYESTER FILM, BACK SHEET FOR SOLAR CELL MODULE, AND SOLAR CELL MODULE

CROSS-REFERENCE TO RELATED APPLICATIONS

This application is a continuation application of International Application No. PCT/JP2013/062184, filed Apr. 25, 2013, which was published under PCT article 21(2) in Japanese, which in turn claims the benefit of priority from Japanese Patent Application No. 2012-113227, filed on May 17, 2012, and Japanese Patent Application No. 2012-180258, filed on Aug. 15, 2012, the disclosures of all of which Applications are incorporated by reference herein in their entirety.

BACKGROUND OF THE INVENTION

Field of the Invention

The present invention relates to a cyclic carbodiimide compound, a polyester film using the cyclic carbodiimide compound, a back sheet for a solar cell module, and a solar cell module.

Background Art

A solar cell module generally has a laminate structure in which a transparent filling material (which is hereinafter also referred to as a sealing material)/a photovoltaic cell/a sealing material/a back sheet (which is hereinafter also referred to as BS) are laminated in this order on a glass or front sheet on the light-receiving surface side to which sunlight is incident. Specifically, the photovoltaic cell is generally embedded with a resin (sealing material) such as EVA (an ethylene-vinyl acetate copolymer) and the like, and protective sheet for a solar cell is adhered thereto. Further, as this protective sheet for a solar cell, a polyester film, in particular, a polyethylene terephthalate (which is hereinafter also referred to as PET) film has been used.

However, the protective sheet for a solar cell, above all, a back sheet (BS) for a solar cell module, which becomes in particular an outermost layer, is considered to be under an environment exposed to weather outdoor for a long period of time, and therefore, excellent weather resistance is required.

Here, a polyester film such as PET and the like, which is also used as a back sheet for a solar cell module has excellent heat resistance, mechanical characteristics, chemical resistance, and the like, and therefore, is widely used industrially. However, it still needs to be improved. As the technology for improving the characteristics of the polyester film in this manner, it is known that by reacting a carbodiimide compound with a terminal carboxyl group of polyester, hydrolysis resistance is improved, and applications to a PET film for a solar cell back sheet or the like have been studied. However, since a general carbodiimide compound generates isocyanate having a low molecular weight by reaction with a terminal carboxyl group of polyester, irritant gases volatilize in the production step, and thus, it has become a problem.

In recent years, a cyclic carbodiimide compound is proposed, and it is reported that when producing a film in a melt state by adding polyester, it is possible to suppress isocyanate gas (refer to Patent Literatures 1 and 2). In Patent Literatures 1 and 2, it is described that since isocyanate which is generated by a reaction with a terminal carboxyl group of polyester is linked to a terminal of polyester, the cyclic carbodiimide can suppress volatilization of isocyanate gas.

CITATION LIST

Patent Literatures

Patent Literature 1: WO 2010/071211
Patent Literature 2: JP-A-2011-258641

SUMMARY OF INVENTION

On the other hand, though a polyester film used in a solar cell module is required to have a high partial discharge voltage, with the increase of a required power generation output, when film production stability is poor and a portion having a thin film thickness partially exists, the partial discharge voltage is significantly lowered. For this reason, a polyester film used in a solar cell module is required to have the film production stability, that is, film thickness uniformity.

However, when the present inventors of the present invention produced a biaxially oriented polyester film by using the cyclic carbodiimide described in Patent Literatures 1 and 2, it was found that an isocyanate group linked to a polyester terminal has high reactivity with a hydroxyl group terminal of polyester, and as long as a known cyclic carbodiimide is used, viscosity of the polyester is significantly increased, and thus the polyester is difficult to use.

The present invention has been made taking this situation into consideration, and it is a problem to be solved by the present invention to provide a polyester film which does not contain isocyanate having a low molecular weight, and has good film thickness uniformity without increase in viscosity. In addition, it is possible to provide a cyclic carbodiimide compound which can be used for the production of the polyester film as described above, can suppress increase in viscosity, and suppress generation of isocyanate gas during the film production.

The inventors of the present invention have found that by using a compound which includes a cyclic structure in which both first nitrogen and second nitrogen in a carbodiimide group are adjacent to arylene groups, and the arylene groups are bonded to each other by a bonding group, and has a specific bulky substituent at an ortho-position with respect to the carbodiimide group in the arylene group, it is possible to suppress generation of isocyanate gas, and by suppressing the reaction between isocyanate linked to the terminal of the polyester and a hydroxyl group terminal of the polyester, it is possible to suppress increase in viscosity during the film production, thereby providing the present invention having the following configurations.

[1] A cyclic carbodiimide compound which is represented by the following Formula (O-1) or (O-2).

Formula (O-1)

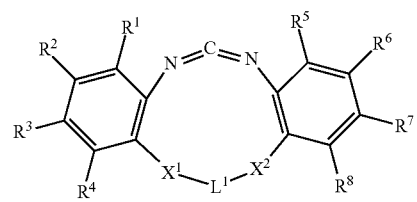

In Formula (O-1), each of $R^4$ and $R^5$ independently represents an alkyl group, an aryl group, or an alkoxy group. Each of $R^2$ to $R^4$ and $R^6$ to $R^8$ independently represents a hydrogen atom, an alkyl group, an aryl group, or an alkoxy group. $R^1$ to $R^8$ may be bonded to each other to form a ring. Each of $X^1$ and $X^2$ independently represents a single bond, —O—, —CO—, —S—, —SO$_2$—, —NH—, or —CH$_2$—. $L^1$ represents a divalent linking group.

Formula (0-2)

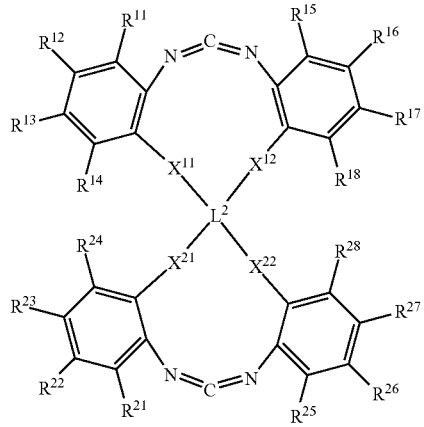

In Formula (O-2), each of $R^{11}$, $R^{15}$, $R^{21}$, and $R^{25}$ independently represents an alkyl group, an aryl group, or an alkoxy group. Each of $R^{12}$ to $R^{14}$, $R^{16}$ to $R^{18}$, $R^{22}$ to $R^{24}$, and $R^{26}$ to $R^{28}$ independently represents a hydrogen atom, an alkyl group, an aryl group, or an alkoxy group. $R^{11}$ to $R^{28}$ may be bonded to each other to form a ring. Each of $X^{11}$, $X^{12}$, $X^{21}$, and $X^{22}$ independently represents a single bond, —O—, —CO—, —S—, —SO$_2$—, —NH—, or —CH$_2$—. $L^2$ represents a tetravalent linking group.

[2] The cyclic carbodiimide compound according to [1], in which both $R^2$ and $R^6$ in Formula (O-1) are preferably hydrogen atoms.

[3] The cyclic carbodiimide compound according to [1] or [2], in which each of $R^1$, $R^5$, $R^{11}$, $R^{15}$, $R^{21}$, and $R^{25}$ in Formulas (O-1) and (O-2) preferably independently represents a secondary or tertiary alkyl group, or an aryl group.

[4] A polyester film including the cyclic carbodiimide compound which is represented by the following Formula (O-1) or (O-2) and polyester.

Formula (O-1)

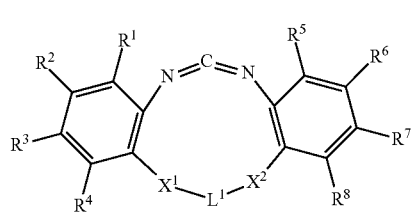

In Formula (O-1), each of $R^4$ and $R^5$ independently represents an alkyl group, an aryl group, or an alkoxy group. Each of $R^2$ to $R^4$ and $R^6$ to $R^8$ independently represents a hydrogen atom, an alkyl group, an aryl group, or an alkoxy group. $R^1$ to $R^8$ may be bonded to each other to form a ring. Each of $X^1$ and $X^2$ independently represents a single bond, —O—, —CO—, —S—, —SO$_2$—, —NH—, or —CH$_2$—. $L^1$ represents a divalent linking group.

Formula (0-2)

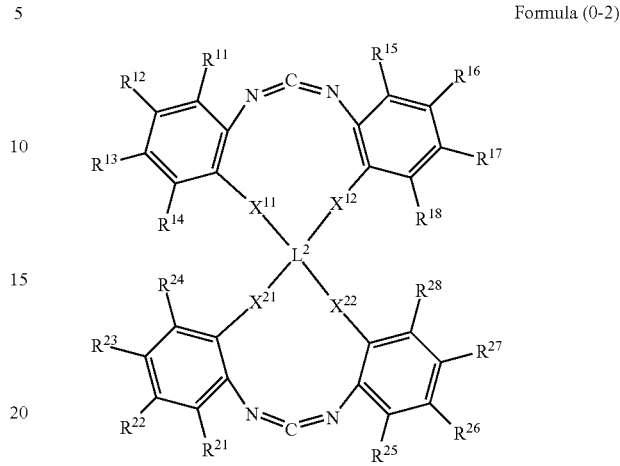

In Formula (O-2), each of $R^{11}$, $R^{15}$, $R^{21}$, and $R^{25}$ independently represents an alkyl group, an aryl group, or an alkoxy group. Each of $R^{12}$ to $R^{14}$, $R^{16}$ to $R^{18}$, $R^{22}$ to $R^{24}$, and $R^{26}$ to $R^{28}$ independently represents a hydrogen atom, an alkyl group, an aryl group, or an alkoxy group. $R^{11}$ to $R^{28}$ may be bonded to each other to form a ring. Each of $X^{11}$, $X^{12}$, $X^{21}$, and $X^{22}$ independently represents a single bond, —O—, —CO—, —S—, —SO$_2$—, —NH—, or —CH$_2$—. $L^2$ represents a tetravalent linking group.

[5] The polyester film according to [4], in which both $R^2$ and $R^6$ in Formula (O-1) are preferably hydrogen atoms.

[6] The polyester film according to [4] or [5], in which each of $R^1$, $R^5$, $R^{11}$, $R^{15}$, $R^{21}$, and $R^{25}$ in Formulas (O-1) and (O-2) preferably independently represents a secondary or tertiary alkyl group, or an aryl group.

[7] The polyester film according to any one of [4] to [6] including the cyclic carbodiimide compound in an amount of 0.05% by mass to 5% by mass relative to 100% by mass of the polyester.

[8] The polyester film according to any one of [4] to [7], in which a component derived from carboxylic acid in the polyester is preferably a component derived from an aromatic dibasic acid or its derivative for forming an ester.

[9] The polyester film according to any one of [4] to [8], which is preferably biaxially oriented.

[10] A back sheet for a solar cell module using the polyester film according to any one of [4] to [9].

[11] A solar cell module using the back sheet for a solar cell module according to [10].

According to the present invention, it is possible to provide a polyester film which does not include isocyanate having a low molecular weight, and has good film thickness uniformity without increase in viscosity. In addition, it is possible to provide a cyclic carbodiimide compound which can be used for the production of the polyester film of the present invention as described above, can suppress increase in viscosity, and suppress generation of isocyanate gas during the film production.

DESCRIPTION OF EMBODIMENTS

Hereinafter, the polyester film, the back sheet for a solar cell module, and the solar cell module of the present invention will be described in detail.

The description of the constitutive elements as described below is based on typical embodiments of the present invention, but the present invention should not be limited thereto. Further, the numerical range expressed by the wording "(a lower limit) to (an upper limit)" means a range that falls between the former number indicating the lower limit of the range and the latter number indicating the upper limit thereof.

Moreover, as isocyanate having a low molecular weight, isocyanate having a molecular weight of 300 or less can be exemplified, however, the present invention is not limited to the range of the molecular weight.

[Polyester Film]

The polyester film of the present invention (hereinafter, also referred to the film of the present invention) includes the cyclic carbodiimide compound which is represented by the following Formula (O-1) or (O-2) and polyester.

Formula (O-1)

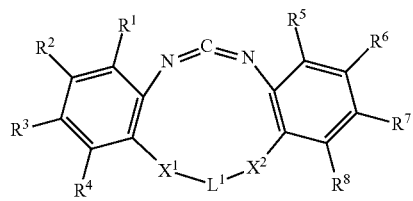

In Formula (O-1), each of $R^4$ and $R^5$ independently represents an alkyl group, an aryl group, or an alkoxy group. Each of $R^2$ to $R^4$ and $R^6$ to $R^8$ independently represents a hydrogen atom, an alkyl group, an aryl group, or an alkoxy group. $R^1$ to $R^8$ may be bonded to each other to form a ring. Each of $X^1$ and $X^2$ independently represents a single bond, —O—, —CO—, —S—, —SO$_2$—, —NH—, or —CH$_2$—. $L^1$ represents a divalent linking group.

Formula (O-2)

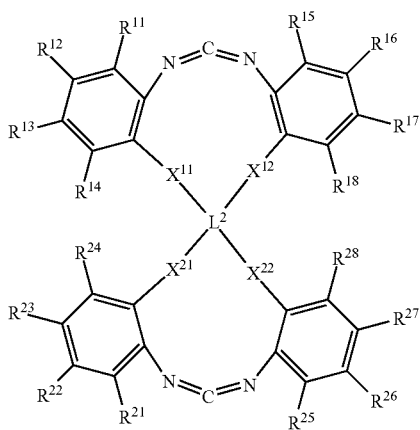

In Formula (O-2), each of $R^{11}$, $R^{15}$, $R^{21}$, and $R^{25}$ independently represents an alkyl group, an aryl group, or an alkoxy group. Each of $R^{12}$ to $R^{14}$, $R^{16}$ to $R^{18}$, $R^{22}$ to $R^{24}$, and $R^{26}$ to $R^{28}$ independently represents a hydrogen atom, an alkyl group, an aryl group, or an alkoxy group. $R^{11}$ to $R^{28}$ may be bonded to each other to form a ring. Each of $X^{11}$, $X^{12}$, $X^{21}$, and $X^{22}$ independently represents a single bond, —O—, —CO—, —S—, —SO$_2$—, —NH—, or —CH$_2$—. $L^2$ represents a tetravalent linking group.

It is also not to be bound by any theory, it is assumed that when melt-extruding a composition including polyester and a carbodiimide compound at about 280° C., for example, when using cyclic aromatic carbodiimide known in the art as a PET terminal blocking agent, (1) a reaction between carbodiimide group and PET-COOH and (2) a reaction between an isocyanate group and PET-OH take place as the following reaction scheme, increase in viscosity occurs, and gel is generated.

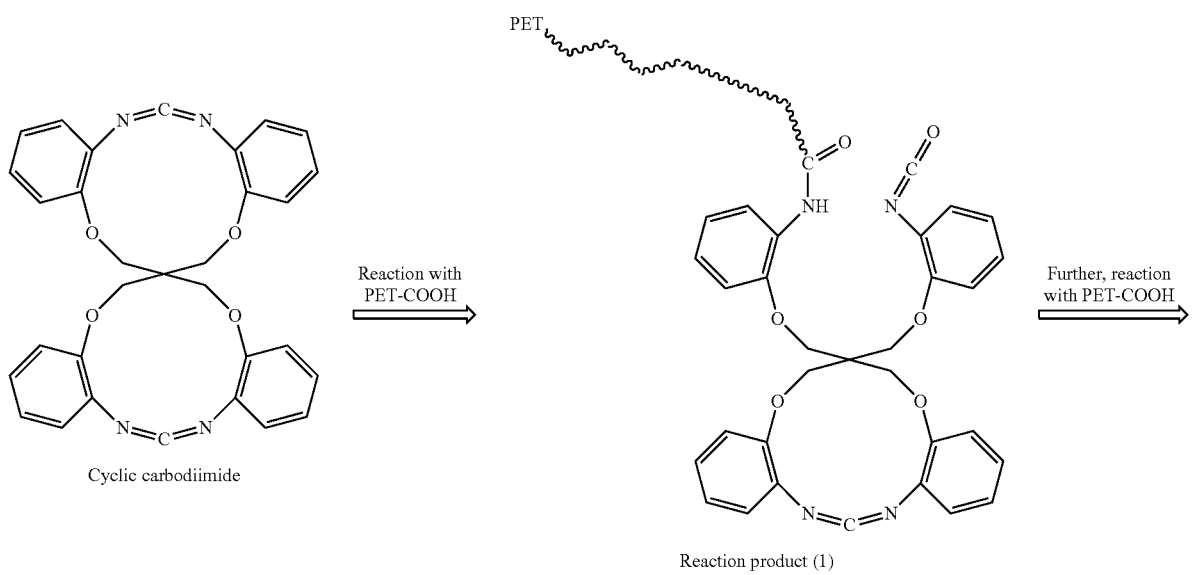

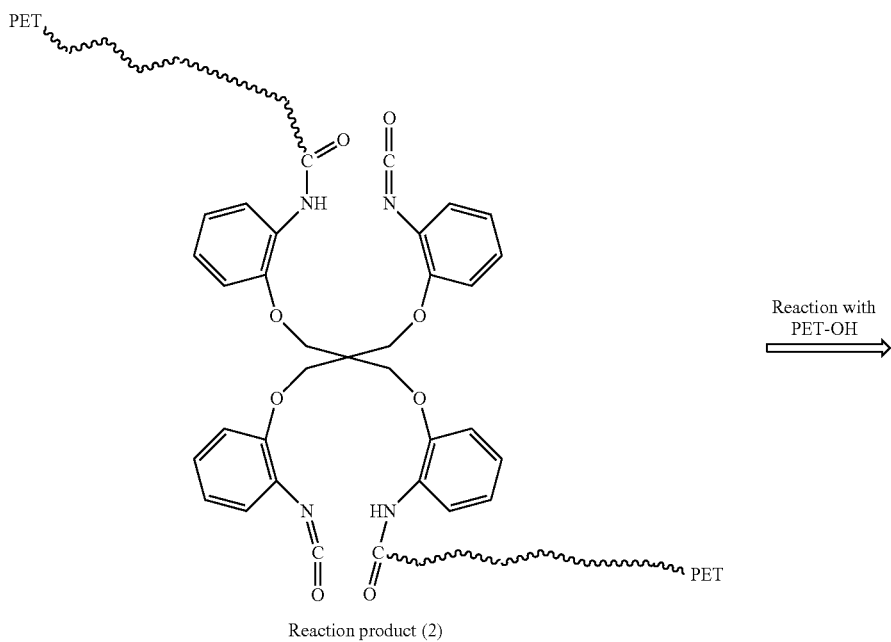
Reaction product (2)
Reaction with PET-OH ⟹
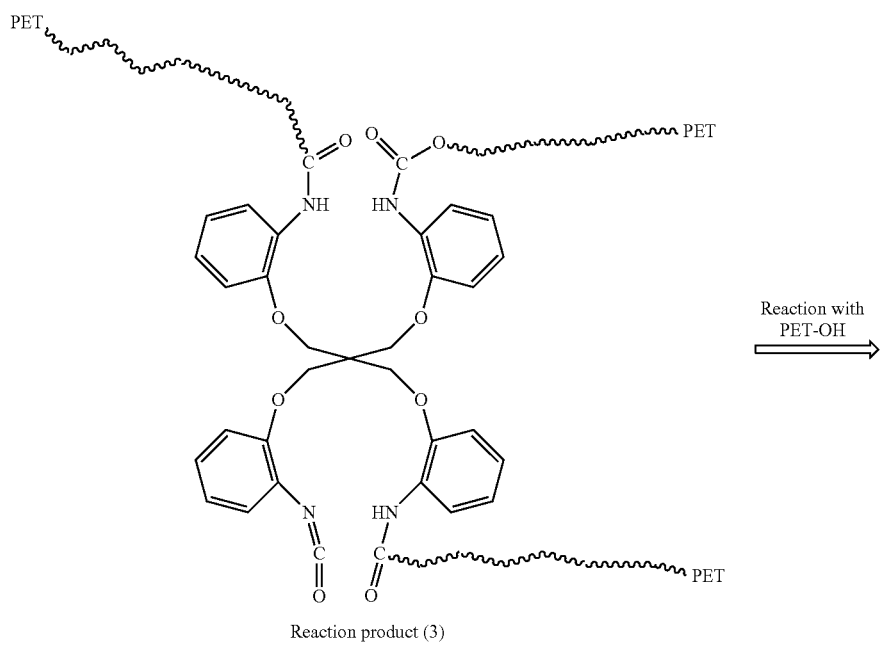
Reaction product (3)
Reaction with PET-OH ⟹

-continued

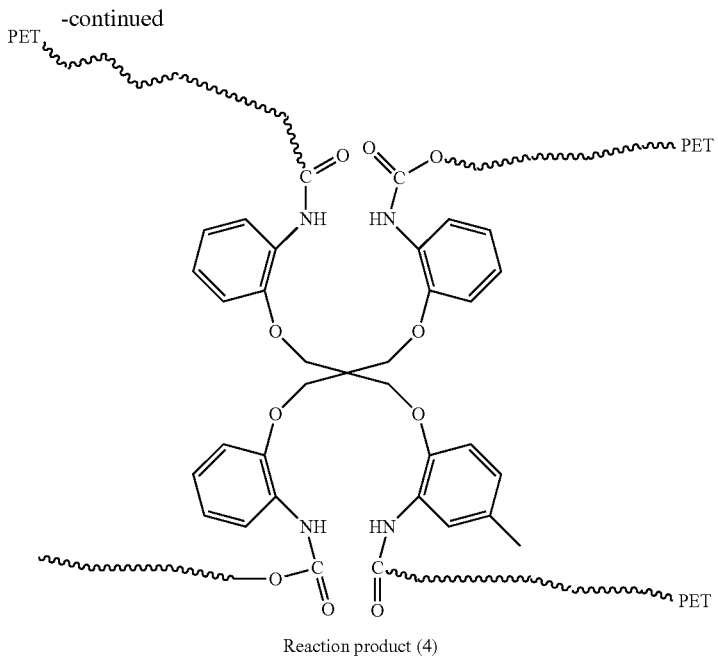

Reaction product (4)

The increase in viscosity and the generation of gel according to the above-described reaction scheme become factors that adversely affect the film thickness uniformity of the obtained polyester film.

In contrast, it was found that by producing a polyester film using a cyclic carbodiimide compound having a specific bulky substituent at an ortho-position with respect to a carbodiimide group of an arylene group adjacent to the carbodiimide, the polyester film having the configuration of the present invention can suppress the reaction with PET-OH in the above reaction scheme, and it is possible to suppress adverse effects on the film thickness uniformity when adding a cyclic carbodiimide compound. As a result, it is possible to provide a polyester film which does not include isocyanate having a low molecular weight, and has good film thickness uniformity without increase in viscosity. In addition, in a case where isocyanate gas described in the production step is included in the polyester film, there is a problem in that adhesiveness to the functional layer after wet heat aging when used in a back sheet for a solar cell module deteriorates, however, it is possible to solve such a problem by using the cyclic carbodiimide of the present invention.

Hereinafter, a material used in the polyester film of the present invention including the cyclic carbodiimide compound of the present invention, the configuration and characteristics of the polyester film of the present invention, and a method for producing the polyester film of the present invention will be described, however, the present invention is not limited to the following embodiments.

Moreover, within a range not interfering with the effects of the present invention, various additives, for example, a carbodiimidization catalyst, a compatibilizer, a plasticizer, a weathering agent, an antioxidant, a thermal stabilizer, a lubricant, an antistatic agent, a brightener, a colorant, a conductive agent, an ultraviolet absorber, a flame retardant, a flame retardant auxiliary agent, a pigment, a dye, or the like may be added to the polyester film of the present invention.

<Material Used in Polyester Film>
(Polyester)

The polyester film of the present invention includes polyester. The polyester is not particularly limited, and the preferable embodiments will be described below.

The intrinsic viscosity (IV) of the polyester is preferably 0.5 dl/g to 0.9 dl/g from the viewpoint of achieving both hydrolysis resistance and film thickness uniformity. By setting the intrinsic viscosity of the polyester to such a range, it is possible reduce the number of polyester terminals, that is, the crosslinking point, and it is possible to suppress gel formation.

The intrinsic viscosity is preferably 0.55 dl/g to 0.85 dl/g, and particularly preferably 0.6 dl/g to 0.84 dl/g from the viewpoint of suppressing the gel formation, achieving both hydrolysis resistance and film thickness uniformity, setting the intrinsic viscosity after film formation in the preferable range as described later, and stirrability at the time of synthesizing with a carbodiimide described later.

For the intrinsic viscosity (IV) of polyester (IV), in a case where polyester used during the film production is 2 or more types (for example, a case of using the retrieved polyester of JP-A-2011-256337 or the like), the intrinsic viscosity of polyester obtained by mixing all polyester preferably satisfies the above range.

For the intrinsic viscosity (IV) of polyester, polyester is dissolved in ortho-chlorophenol, and from the solution viscosity measured at 25° C., the intrinsic viscosity [η] is obtained by the following equation.

$\eta_{sp}/C=[\eta]+K[\eta]^2 \cdot C$

Here, $\eta_{sp}$ is (solution viscosity/solvent viscosity)−1, C is the dissolved polymer weight per 100 ml of solvent (1 g/100 ml in this measurement), K is Huggins constant (0.343), and the solution viscosity and the solvent viscosity are measured using an Ostwald viscometer.

The polyester is preferably saturated polyester.

By using such saturated polyester, it is possible to obtain an excellent polyester film compared to the film using unsaturated polyester from the viewpoint of dynamic strength.

The polyester has a —COO— bond or a —OCO— bond in the middle of the polymer. In addition, the terminal group of the polyester is preferably a linear saturated polyester synthesized from an aromatic dibasic acid or its derivative capable of forming an ester, a diol or an derivative for forming an ester thereof as an OH group, a COOH group, or a protected group thereof (an $OR^X$ group, a $COOR^X$ group ($R^X$ is any substituent such as an alkyl group). As the linear saturated polyester, for example, those described in 2009-155479 or JP-A-2010-235824 can be suitably used.

Specific examples of the linear saturated polyester include polyethylene terephthalate (PET), polyethylene isophthalate, polybutylene terephthalate, poly(1,4-cyclohexylenedimethylene terephthalate), polyethylene-2,6-naphthalate, and among these, polyethylene terephthalate or polyethylene-2,6-naphthalate is particularly preferable, and polyethylene terephthalate is more particularly preferable from the viewpoint of the balance between the mechanical properties and the cost. Moreover, whereas a film of polyethylene-2,6-naphthalate or polybutylene terephthalate is produced in a melt state by heating to 230° C. or higher during the film production, a film of PET is produced in a melt state by heating to 250° C. or higher, and thus isocyanate is further easily generated, and in the polyester film of the present invention, it is possible to reduce the residual amount of isocyanate even in a case where the polyester (A) is PET.

The polyester may be a homopolymer or a copolymer. Furthermore, it may be a blend of the polyester with a small amount of any other type of resin, for example, polyimide, or the like. In addition, it is also possible to use a crystalline polyester which can form anisotropy during the melting as the polyester.

The terminal carboxyl group content in the polyester (the carboxylic acid value of the polyester, hereinafter, referred to as AV) is preferably 25 eq/ton or less, more preferably 20 eq/ton or less, particularly preferably 16 eq/ton or less, and more particularly preferably 15 eq/ton or less with respect to the polyester. If the carboxyl group content is 25 eq/ton or less, the hydrolysis resistance of polyester film and heat resistance by combination with the cyclic carbodiimide compound are maintained, and thus, reduction of strength at a time of wet heat aging can be suppressed low. The lower limit of the terminal carboxyl group content is desirably 10 eq/ton or greater from the viewpoint of keeping the adhesiveness (adhesive property) among layers (for example, a white layer) formed when the polyester film of the present invention is used as the back sheet for a solar cell module. The terminal carboxyl group content in the polyester can be adjusted by the kind of a polymerization catalyst, the polymerization time, or the film formation conditions (the film formation temperature and time). The carboxyl group content can be measured by a titration method according to the method described in H. A. Pohl, Anal. Chem. 26 (1954) 2145. Specifically, a polyester is dissolved in benzyl alcohol at 205° C. and a phenol red indicator is added. Then, titration is performed with a water/methanol/benzyl alcohol solution of sodium hydroxide, and from the titration amount, the carboxylic acid value (eq/ton) can be calculated.

The terminal hydroxyl group content in the polyester is preferably 120 eq/ton or less, and more preferably 90 eq/ton or less, with respect to the polyester. If the hydroxyl group content is 120 eq/ton or less, the reaction between cyclic carbodiimide having a bulky functional group at a specific position described later and the hydroxyl group is suppressed, and thus, the reaction with a carboxyl group is preferentially undergone, which can further reduce the carboxylic acid value. The lower limit of the hydroxyl group content is desirably 20 eq/ton from the viewpoint of adhesiveness with an upper layer. The hydroxyl group content in the polyester can be adjusted by the kind of a polymerization catalyst, the polymerization time, or the film formation conditions (the film formation temperature and time). For the terminal hydroxyl group content, a value measured by $^1$H-NMR, using a deuterated hexafluoroisopropanol solvent, can be used.

For the molecular weight of the polyester, the weight average molecular weight (Mw) is preferably 5,000 to 30,000, more preferably 8,000 to 26,000, and particularly preferably 12,000 to 24,000 from the viewpoint of heat resistance and viscosity. As the weight average molecular weight of the polyester, a value in terms of polymethyl methacrylate (PMMA), measured by gel permeation chromatography (GPC) using hexafluoroisopropanol as a solvent, can be used.

The polyester can be synthesized according to a known method. For example, polyester can be synthesized according to a known polycondensation method, a ring-opening polymerization method, or the like, which can be applied to any one of the reactions by transesterification reaction and direct polymerization.

In a case where the polyester used in the present invention is a polymer or copolymer, obtained by the condensation reaction of an aromatic dibasic acid or its derivative capable of forming an ester with a diol or an derivative for forming an ester thereof as a main components, the polyester can be produced by subjecting an aromatic dibasic acid or its derivative capable of forming an ester thereof, and a diol or an derivative for forming an ester thereof to esterification reaction or transesterification reaction, and then to polycondensation reaction. Further, by selecting the raw material or the reaction condition, the carboxylic acid value or the intrinsic viscosity of the polyester can be controlled. Further, in order to perform the esterification or transesterification reaction and the polycondensation reaction effectively, it is preferable to add a polymerization catalyst during these reactions.

As a polymerization catalyst in the polymerization of the polyester, an Sb-based, Ge-based, or Ti-based compound is preferably used from the viewpoint of inhibiting the carboxyl group content to a predetermined range or less. Among these, a Ti-based compound is particularly preferable. In the case of using a Ti-based compound, the Ti-based compound is used as the catalyst in the range of the amount of 1 ppm to 30 ppm, and more preferably 3 ppm to 15 ppm to perform polymerization. If the proportion of the Ti-based compound is within the range, it is possible to adjust the terminal carboxyl groups to fall within the range as described below, and it is also possible to keep the hydrolysis resistance of the polymer substrate low.

In the synthesis of the polyester using a Ti-based compound, for example, the methods described in JP-B-8-301198, Japanese Patent Nos. 2543624, 3335683, 3717380, 3897756, 3962226, 3979866, 3996871, 4000867, 4053837, 4127119, 4134710, 4159154, 4269704, 4313538, or the like may be applied.

Preferably, the polyester is one subjected to solid-phase polymerization after polymerization. This can result in the preferable carboxylic acid value. The solid-phase polymerization may be in a continuous method (where the resin is filled in a tower, gradually circulated therein with heating for a predetermined period of time, and then discharged) or in a batch method (where the resin is put into a container and heated therein for a predetermined period of time). Specifically, the methods described in Japanese Patents 2621563, 3121876, 3136774, 3603585, 3616522, 3617340, 3680523, 3717392, 4167159, or the like may be applied to the solid-phase polymerization.

The temperature of the solid-phase polymerization is preferably 170° C. to 240° C., more preferably from 180° C. to 230° C., and even more preferably 190° C. to 220° C. The time of the solid-phase polymerization is preferably 5 hours to 100 hours, more preferably 10 hours to 75 hours, and even more preferably 15 hours to 50 hours. The solid-phase polymerization is preferably performed in vacuum or in a nitrogen atmosphere.

(Cyclic Carbodiimide Compound)

The polyester film of the present invention includes the cyclic carbodiimide compound (hereinafter, also referred to as the cyclic carbodiimide compound of the present invention) which is represented by Formula (O-1) or (O-2).

Hereinafter, the preferable structure of the cyclic carbodiimide compound of the present invention will be described in order of Formulas (O-1) and (O-2).

First, the cyclic carbodiimide compound which is represented by Formula (O-1) will be described.

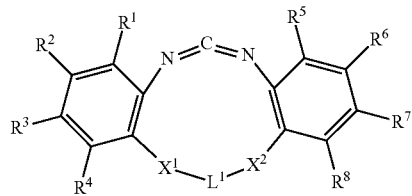

Formula (O-1)

In Formula (O-1), each of $R^4$ and $R^5$ independently represents an alkyl group, an aryl group, or an alkoxy group. Each of $R^2$ to $R^4$ and $R^6$ to $R^8$ independently represents a hydrogen atom, an alkyl group, an aryl group, or an alkoxy group. $R^1$ to $R^8$ may be bonded to each other to form a ring. Each of $X^1$ and $X^2$ independently represents a single bond, —O—, —CO—, —S—, —SO$_2$—, —NH—, or —CH$_2$—. $L^1$ represents a divalent linking group.

In Formula (O-1), each of $R^1$ and $R^5$ independently represents an alkyl group, an aryl group, or an alkoxy group, preferably represents an alkyl group or an aryl group, more preferably represents a secondary or tertiary alkyl group, or an aryl group from the viewpoint of suppressing the reaction of isocyanate linked to the terminal of polyester and the hydroxyl group terminal of polyester and suppressing increase in viscosity, and particularly preferably represent a secondary alkyl group.

The alkyl group which is represented by $R^1$ or $R^5$ is preferably an alkyl group having 1 to 20 carbon atoms, more preferably an alkyl group having 1 to 12 carbon atoms, and particularly preferably an alkyl group having 2 to 6 carbon atoms. The alkyl group which is represented by $R^1$ or $R^5$ may be a linear alkyl group, a branched alkyl group, or a cyclic alkyl group, however, a branched alkyl group or a cyclic alkyl group is preferable from the viewpoint of suppressing the reaction of isocyanate linked to the terminal of polyester and the hydroxyl group terminal of polyester and suppressing increase in viscosity. The alkyl group which is represented by $R^1$ or $R^5$ is preferably a secondary or tertiary alkyl group, and more preferably a secondary alkyl group. Examples of the alkyl group which is represented by $R^1$ or $R^2$ include a methyl group, an ethyl group, an n-propyl group, a sec-propyl group, an iso-propyl group, an n-butyl group, a tert-butyl group, a sec-butyl group, an iso-butyl group, an n-pentyl group, a sec-pentyl group, an iso-pentyl group, an n-hexyl group, a sec-hexyl group, an iso-hexyl group, and a cyclohexyl group, and among these, an iso-propyl group, a tert-butyl group, an iso-butyl group, an iso-pentyl group, an iso-hexyl group, and a cyclohexyl group are preferable, an iso-propyl group, a cyclohexyl group, and a tert-butyl group are more preferable, and an iso-propyl group and a cyclohexyl group are particularly preferable.

The alkyl group which is represented by $R^1$ or $R^5$ may further have a substituent, and the substituent is not particularly limited. However, the alkyl group which is represented by $R^1$ or $R^5$ preferably does not further have a substituent from the viewpoint of reactivity with carboxylic acid.

The aryl group which is represented by $R^1$ or $R^5$ is preferably an aryl group having 6 to 20 carbon atoms, more preferably an aryl group having 6 to 12 carbon atoms, and particularly preferably an aryl group having 6 carbon atoms. The aryl group which is represented by $R^1$ or $R^5$ may be an aryl group formed by condensation of $R^1$ and $R^2$ or $R^5$ and $R^6$, and each of $R^1$ and $R^5$ preferably does not form a ring by condensation with $R^2$ or $R^6$. Examples of the aryl group which is represented by $R^1$ or $R^5$ include a phenyl group and a naphthyl group or the like, and among these, a naphthyl group is more preferable.

The aryl group which is represented by $R^1$ or $R^5$ may further have a substituent, and the substituent is not particularly limited. However, the aryl group which is represented by $R^1$ or $R^5$ preferably does not further have a substituent from the viewpoint of reactivity with carboxylic acid.

The alkoxy group which is represented by $R^1$ or $R^5$ is preferably an alkoxy group having 1 to 20 carbon atoms, more preferably an alkoxy group having 1 to 12 carbon atoms, and particularly preferably an alkoxy group having 2 to 6 carbon atoms. The alkoxy group which is represented by $R^1$ or $R^5$ may be a linear alkoxy group, a branched alkoxy group, or a cyclic alkoxy group, however, a branched alkoxy group or a cyclic alkoxy group is preferable from the viewpoint of suppressing the reaction of isocyanate linked to the terminal of polyester and the hydroxyl group terminal of polyester and suppressing increase in viscosity. Preferable example of an alkoxy group which is represented by $R^1$ or $R^5$ is a group in which —O— is linked to the terminal of an alkyl group which is represented by $R^1$ or $R^5$, and preferable range is also the same as that of a group in which —O— is linked to the terminal of a preferable alkyl group which is represented by $R^1$ or $R^5$.

The alkoxy group which is represented by $R^1$ or $R^5$ may further have a substituent, and the substituent is not particularly limited. However, the alkoxy group which is represented by $R^1$ or $R^5$ preferably does not further have a substituent from the viewpoint of reactivity with carboxylic acid.

$R^1$ and $R^5$ may be the same as or different from each other, and are preferably the same from the viewpoint of cost.

In Formula (O-1), each of $R^2$ to $R^4$ and $R^6$ to $R^8$ independently represents a hydrogen atom, an alkyl group, an aryl group, or an alkoxy group, and a hydrogen atom, an alkyl group having 1 to 20 carbon atoms, and an alkoxy group having 1 to 20 carbon atoms are preferable, a hydrogen atom and, an alkyl group having 1 to 6 carbon atoms are more preferable, and a hydrogen atom is particularly preferable.

The alkyl group, the aryl group, or the alkoxy group which is represented by $R^2$ to $R^4$ or $R^6$ to $R^8$ may further have a substituent, and the substituent is not particularly limited.

In the cyclic carbodiimide compound of the present invention, both $R^2$ and $R^6$ in Formula (O-1) are preferably hydrogen atoms from the viewpoint of ease of introducing a bulky substituent to $R^1$ and $R^5$. Here, in p. 15 and p. 14 of WO2010/071211, a compound in which a site (meta-position with respect to the carbodiimide group) corresponding to $R^2$ or $R^6$ in Formula (O-1) are substituted with an alkyl group or an aryl group is illustrated, however, these compounds cannot suppress the reaction of isocyanate linked to the terminal of polyester and the hydroxyl group terminal of polyester, and introduction of a substituent to a site (ortho-position with respect to the carbodiimide group) corresponding to $R^2$ or $R^6$ in Formula (O-1) is difficult.

In Formula (O-1), $R^1$ to $R^8$ may be bonded to each other to form a ring. The ring formed at this time is not particularly limited, and aromatic ring is preferable. For example, two or more of $R^1$ to $R^4$ may be bonded to each other to form a condensed ring, and may form an arylene group or a heteroarylene group having 10 or more carbon atoms with a benzene ring in which $R^1$ to $R^4$ are substituted. As the arylene group having 10 or more carbon atoms formed at this time, an aromatic group having 10 to 15 carbon atoms such as a naphthalenediyl group or the like can be exemplified.

In the same manner, for example, two or more of $R^5$ to $R^8$ may be bonded to each other to form a condensed ring, $R^5$ to $R^8$ may form an arylene group or a heteroarylene group having 10 or more carbon atoms with a benzene ring in which $R^5$ to $R^8$ are substituted and the preferable range at this time is the same as the preferable range when forming an arylene group or a heteroarylene group having 10 or more carbon atoms with a benzene ring in which $R^1$ to $R^4$ are substituted.

However, in the cyclic carbodiimide compound of the present invention, $R^1$ to $R^8$ in Formula (O-1) preferably does not form a ring by bonding to each other.

In Formula (O-1), each of $X^1$ and $X^2$ independently represents at least one type selected from a single bond, —O—, —CO—, —S—, —SO$_2$—, —NH—, or —CH$_2$—, and among these, preferably —O—, —CO—, —S—, —SO$_2$—, or —NH—, more preferable —O—, or —S— from the viewpoint of ease of synthesis.

In Formula (O-1), $L^1$ represents a divalent linking group, and is preferably a divalent aliphatic group having 1 to 20 carbon atoms, a divalent alicyclic group having 3 to 20 carbon atoms, a divalent aromatic group having 5 to 15 carbon atoms which may include a heteroatom or a substituent, respectively, or a combination of these, and more preferably a divalent aliphatic group having 1 to 20 carbon atoms.

As a divalent aliphatic group which is represented by $L^1$, an alkylene group having 1 to 20 carbon atoms can be exemplified. Examples of the alkylene group having 1 to 20 carbon atoms include a methylene group, an ethylene group, a propylene group, a butylene group, a pentylene group, a hexylene group, a heptylene group, an octylene group, a nonylene group, a decylene group, a dodecylene group, and hexadecylene group, and a methylene group, an ethylene group, and a propylene group is more preferable, and an ethylene group is particularly preferable. These aliphatic groups may be substituted. Examples of the substituents include an alkyl group having 1 to 20 carbon atoms, an aryl group having 6 to 15 carbon atoms, a halogen atom, a nitro group, an amide group, a hydroxyl group, an ester group, an ether group, and an aldehyde group.

As a divalent alicyclic group which is represented by $L^1$, a cycloalkylene group having 3 to 20 carbon atoms can be exemplified. Examples of the cycloalkylene group having 3 to 20 carbon atoms include a cyclopropylene group, a cyclobutylene group, a cyclopentylene group, a cyclohexylene group, a cycloheptylene group, a cyclooctylene group, a cyclononylene group, a cyclodecylene group, a cyclododecylene group, and a cyclohexadecylene group. These alicyclic groups may be substituted. Examples of the substituents include an alkyl group having 1 to 20 carbon atoms, an aryl group having 6 to 15 carbon atoms, a halogen atom, a nitro group, an amide group, a hydroxyl group, an ester group, an ether group, and an aldehyde group.

As a divalent aromatic group which is represented by $L^1$, an arylene group having 5 to 15 carbon atoms which may have a heterocyclic structure by including a heteroatom can be exemplified. Examples of the arylene group having 5 to 15 carbon atoms include a phenylene group and a naphthalenediyl group. These aromatic groups may be substituted. Examples of the substituents include an alkyl group having 1 to 20 carbon atoms, an aryl group having 6 to 15 carbon atoms, a halogen atom, a nitro group, an amide group, a hydroxyl group, an ester group, an ether group, and an aldehyde group.

In Formula (O-1), the number of atoms in a cyclic structure which includes a carbodiimide group is preferably 8 to 50, more preferably 10 to 30, still more preferably 10 to 20, and particularly preferably 10 to 15.

Here, the number of atoms in the cyclic structure which includes a carbodiimide group means the number of atoms which directly configure the cyclic structure which includes a carbodiimide group, and for example, when the cyclic structure is an eight-membered ring, the number of atoms is 8, and when the cyclic structure is a fifty-membered ring, the number of atoms is 50. This is because in a case where the number of atoms in the cyclic structure is 8 or less, stability of a cyclic carbodiimide compound is reduced, and there are cases where storage and usage become difficult. In addition, from the viewpoint of reactivity, the upper limit value of the number of membered-ring is not particularly limited, however, in a case of a cyclic carbodiimide compound having the number of atoms greater than 50, a case where cost is significantly increased due to the difficulty in synthesis occurs. From these viewpoints, in Formula (O-1), the range of the number of atoms in the cyclic structure is preferably 10 to 30, more preferably 10 to 20, and particularly preferably 10 to 15.

Next, the cyclic carbodiimide compound which is represented by Formula (O-2) will be described.

Formula (O-2)

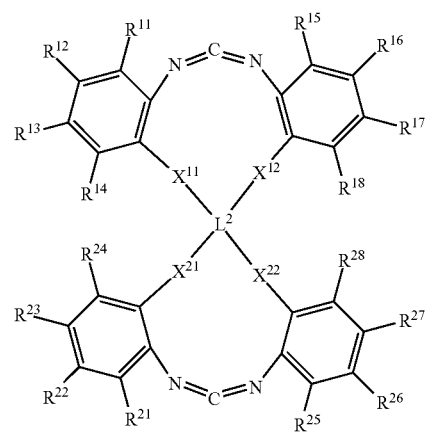

In Formula (O-2), each of $R^{11}$, $R^{15}$, $R^{21}$, and $R^{25}$ independently represents an alkyl group, an aryl group, or an alkoxy group. Each of $R^{12}$ to $R^{14}$, $R^{16}$ to $R^{18}$, $R^{22}$ to $R^{24}$, and $R^{26}$ to $R^{28}$ independently represents a hydrogen atom, an alkyl group, an aryl group, or an alkoxy group. $R^{11}$ to $R^{28}$ may be bonded to each other to form a ring. Each of $X^{11}$, $X^{12}$, $X^{21}$, and $X^{22}$ independently represents a single bond, —O—, —CO—, —S—, —SO$_2$—, —NH—, or —CH$_2$—. $L^2$ represents a tetravalent linking group.)

The preferable range of $R^{11}$, $R^{15}$, $R^{21}$, and $R^{25}$ in Formula (O-2) is the same as the preferable range of $R^1$ and $R^5$ in Formula (O-1). The aryl group which is represented by $R^{11}$, $R^{15}$, $R^{21}$, or $R^{25}$ may be an aryl group formed by condensation of $R^{11}$ and $R^{12}$, condensation of $R^{15}$ and $R^{16}$, condensation of $R^{21}$ and $R^{22}$, or condensation of $R^{25}$ and $R^{26}$, and each of $R^{11}$, $R^{15}$, $R^{21}$, or $R^{25}$ preferably does not form a ring by condensation with $R^{12}$, $R^{16}$, $R^{22}$, or $R^{26}$.

$R^{11}$, $R^{15}$, $R^{21}$, and $R^{25}$ may be the same as or different from each other, and are preferably the same from the viewpoint of cost.

The preferable range of $R^{12}$ to $R^{14}$, $R^{16}$ to $R^{18}$, $R^{22}$ to $R^{24}$, and $R^{26}$ to $R^{28}$ in Formula (O-2) is the same as the preferable range of $R^2$ to $R^4$ and $R^6$ to $R^8$ in Formula (O-1).

In $R^{12}$ to $R^{14}$, $R^{16}$ to $R^{18}$, $R^{22}$ to $R^{24}$, and $R^{26}$ to $R^{28}$, all of $R^{12}$, $R^{16}$, $R^{22}$, and $R^{26}$ are preferably hydrogen atoms from the viewpoint of ease of introducing a bulky substituent to $R^{11}$, $R^{15}$, $R^{21}$, or $R^{25}$.

In Formula (O-2), $R^{11}$ to $R^{28}$ may be bonded to each other to form a ring, and the preferable range of the ring is the same as the range of the ring formed when $R^1$ to $R^8$ in Formula (O-1) are bonded to each other.

The preferable range of $X^{11}$, $X^{12}$, $X^{21}$, and $X^{22}$ in Formula (O-2) is the same as the preferable range of $X^1$ and $X^2$ in Formula (O-1).

In Formula (O-2), $L^2$ represents a tetravalent linking group, and is preferably a tetravalent aliphatic group having 1 to 20 carbon atoms, a tetravalent alicyclic group having 3 to 20 carbon atoms, a tetravalent aromatic group having 5 to 15 carbon atoms which may include a heteroatom or a substituent, respectively, or a combination of these, and more preferably a tetravalent aliphatic group having 1 to 20 carbon atoms.

As a tetravalent aliphatic group which is represented by $L^2$, an alkanetetrayl group having 1 to 20 carbon atoms and the like can be exemplified. Examples of the alkanetetrayl group having 1 to 20 carbon atoms include a methanetetrayl group, an ethanetetrayl group, a propanetetrayl group, a butanetetrayl group, pentanetetrayl group, a hexanetetrayl group, a heptanetetrayl group, an octanetetrayl group, a nonanetetrayl group, a decanetetrayl group, a dodecanetetrayl group, and a hexadecanetetrayl group, a methanetetrayl group, an ethanetetrayl group, and a propanetetrayl group are more preferable, and an ethanetetrayl group is particularly preferable. These aliphatic groups may include substituents. Examples of the substituents include an alkyl group having 1 to 20 carbon atoms, an aryl group having 6 to 15 carbon atoms, a halogen atom, a nitro group, an amide group, a hydroxyl group, an ester group, an ether group, and an aldehyde group.

As a tetravalent alicyclic group which is represented by $L^2$, a cycloalkanetetrayl group having 3 to 20 carbon atoms can be exemplified. Examples of the cycloalkanetetrayl group having 3 to 20 carbon atoms include a cyclopropanetetrayl group, a cyclobutanetetrayl group, a cyclopentanetetrayl group, a cyclohexanetetrayl group, a cycloheptanetetrayl group, a cyclooctanetetrayl group, a cyclononanetetrayl group, a cyclodecanetetrayl group, a cyclododecanetetrayl group, and a cyclohexadecanetetrayl group. These alicyclic groups may include substituents. Examples of the substituents include an alkyl group having 1 to 20 carbon atoms, an arylene group having 6 to 15 carbon atoms, a halogen atom, a nitro group, an amide group, a hydroxyl group, an ester group, an ether group, and an aldehyde group.

As a tetravalent aromatic group which is represented by $L^2$, an arenetetrayl group having 5 to 15 carbon atoms which may have a heterocyclic structure by including a heteroatom can be exemplified. As the arenetetrayl group (tetravalent) having 5 to 15 carbon atoms, a benzenetetrayl group and a naphthalenetetrayl group can be exemplified. These aromatic groups may be substituted. Examples of the substituents include an alkyl group having 1 to 20 carbon atoms, an aryl group having 6 to 15 carbon atoms, a halogen atom, a nitro group, an amide group, a hydroxyl group, an ester group, an ether group, and an aldehyde group.

In Formula (O-2), two cyclic structure including carbodiimide groups through L2 which is a tetravalent linking group is included.

The preferable range of the number of atoms in the cyclic structure including each carbodiimide group in Formula (O-2) is the same as the preferable range of the number of atoms in the cyclic structure including a carbodiimide group in Formula (0-1), respectively.

The cyclic carbodiimide compound of the present invention is preferably an aromatic carbodiimide that does not have a ring structure in which the first nitrogen and the second nitrogen of two or more carbodiimide groups in a molecule are bonded with a linking group, in other words, an aromatic carbodiimide that is monocyclic, and represented by Formula (O-1) from the viewpoint of difficulty in thickening.

However, from the viewpoint of suppressing volatilization and generation of isocyanate gas during the production, the cyclic carbodiimide compound of the present invention is also preferably a cyclic carbodiimide compound which has a plurality of cyclic structures and is represented by Formula (O-2).

The molecular weight of the cyclic carbodiimide compound of the present invention is preferably 400 or greater since the volatility is low and it is possible to suppress generation of isocyanate gas during the production. In addition, the upper limit of the molecular weight of the cyclic carbodiimide compound of the present invention is not particularly limited as long as it does not impair the effect of the present invention, but from the viewpoint of reactivity with carboxylic acid, the upper limit is preferably 1,500 or less.

The molecular weight of the cyclic carbodiimide compound of the present invention is more preferably 500 to 1,200.

As specific examples of the cyclic carbodiimide compound which is represented by Formula (O-1) or (O-2), that is, specific examples of the cyclic carbodiimide compound of the present invention, the following compounds can be exemplified. However, the present invention is not limited to the following specific examples.

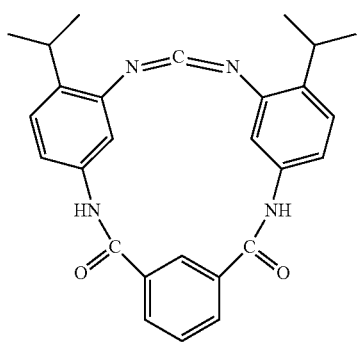
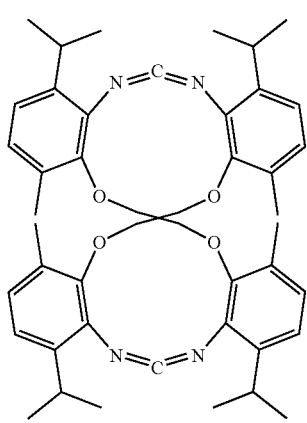
R is a hydrogen atom, an alkyl group, or aryl group
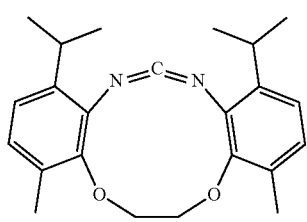
Compound 1
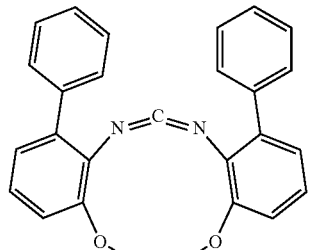
Compound 3
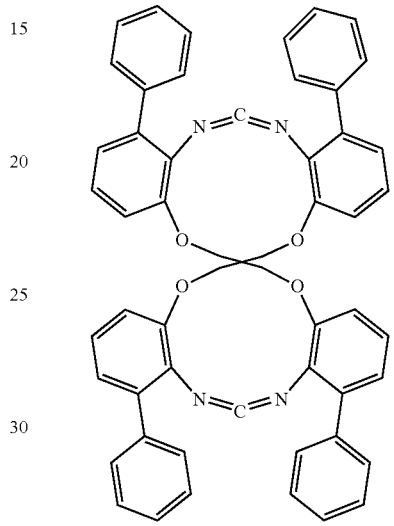
Compound 4
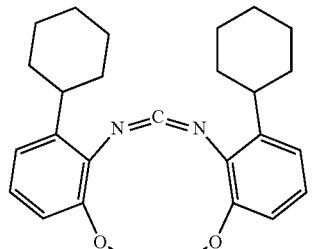
Compound 5
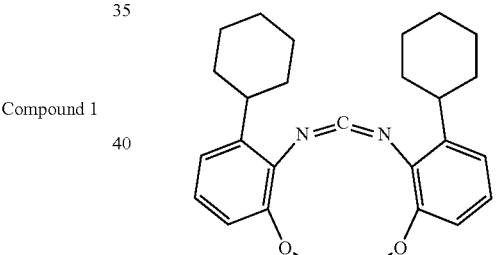
Compound 6
Compound 2

-continued

Compound 7

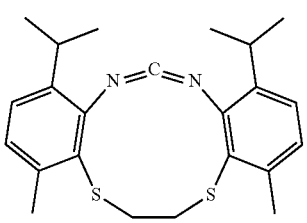

Compound 8

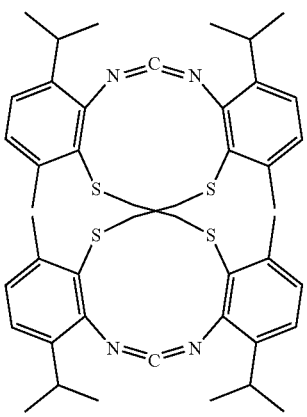

The cyclic carbodiimide compound of the present invention is a compound having at least one structure (carbodiimide group) which is represented by —N=C=N— adjacent to an aromatic ring, and can be produced, for example, by heating an organic isocyanate, in the presence of an appropriate catalyst, to perform a decarboxylation reaction. In addition, the cyclic carbodiimide compound of the present invention can be synthesized by referencing a method described in JP-A-2011-256337.

When synthesizing a cyclic carbodiimide compound of the present invention, as a method for introducing a specific bulky substituent to an ortho-position of an arylene group adjacent to a first nitrogen and a second nitrogen in a carbodiimide group is not particularly limited, and for example, by nitrating alkyl benzene by a known method, it is possible to synthesize nitrobenzene in which the alkyl group is substituted, and it is possible to synthesize a cyclic carbodiimide using the nitrobenzene by a method described in WO2011/158958.

Here, it is also considered that in order to increase the hydrolysis resistance of polyester film, it is preferable to block many carboxyl terminals of polyester. However, when putting a large amount of cyclic carbodiimide compound such as the cyclic carbodiimide compound of the present invention into polyester, gel is formed and the film thickness uniformity of the polyester film is likely to be insufficient. Therefore, by controlling the addition amount of the cyclic carbodiimide compound of the present invention to be a specific range, it is easy to control both hydrolysis resistance and film thickness uniformity of the polyester film to be a preferable range. Moreover, the cyclic polycarbodiimide compound put in a large amount for a secondary reaction remains as the unreacted cyclic carbodiimide compound, and further, it may be reacted with moisture, the terminal group of polyester, or other free acid, and thus to be decomposed into isocyanates in some cases.

The polyester film of the present invention includes the cyclic carbodiimide compound of the present invention in an amount of 0.05% by mass to 5% by mass relative to 100% by mass of the polyester. It is preferable that the polyester film include the cyclic carbodiimide compound of the lower limit value or greater from the viewpoint of improving both hydrolysis resistance and film thickness uniformity. It is preferable that the polyester film include the cyclic carbodiimide compound of the upper limit value or less from the viewpoint of suppressing gelation and improving film thickness uniformity of the polyester film of the present invention.

The polyester film of the present invention more preferably includes the cyclic carbodiimide compound of the present invention in an amount of 0.1% by mass to 2% by mass, and particularly preferably includes 0.1% by mass to 1% by mass, relative to 100% by mass of the polyester.

The polyester film of the present invention does not refuse to include a carbodiimide compound other than the cyclic carbodiimide compound of the present invention as long as it is not contrary to the spirit of the present invention, and 90% or greater of a carbodiimide compound included in the polyester film of the present invention is preferably the cyclic carbodiimide compound of the present invention, 95% or greater is more preferably the cyclic carbodiimide compound of the present invention, and 100% is particularly preferably the cyclic carbodiimide compound of the present invention.

<Configuration and Characteristics of Polyester Film>

The thickness of the polyester film of the present invention varies according to the uses, but in the case where the polyester film is used as a member of a back sheet for a solar cell module, the thickness is preferably 25 μm to 300 μm, and more preferably 120 μm to 300 μm. When the thickness is 25 μm or greater, a sufficient dynamic strength is obtained, whereas a thickness set to be 300 μm or less is advantageous in terms of cost.

The polyester film of the present invention is preferably stretched, more preferably biaxially stretched, and particularly preferably biaxially stretched in plane compared to stretching of a tubular shape, and more particularly preferably sequentially biaxially stretched.

The degree of MD orientation and the degree of TD orientation of the polyester film of the present invention are each preferably 0.14 or greater, more preferably 0.155 or greater, and particularly preferably 0.16 or greater. If each degree of orientation is 0.14 or greater, the restriction of the non-crystalline chain is improved (the mobility is lowered), and the hydrolysis resistance is improved. The degree of MD orientation and the degree of TD orientation can be calculated from the degree of MD orientation: Δn(x−z), TD; Δn(y−z), by measuring the refractive indices in the x, y, and z directions of the biaxially oriented film at an atmosphere at 25° C., using an Abbe refractometer, a monochromatic light sodium D-line as the light source, and methylene iodide as a mounting solution.

In addition, the intrinsic viscosity (IV) of the polyester film of the present invention is preferably 0.70 dl/g to 0.94 dl/g, more preferably 0.71 dl/g to 0.84 dl/g, and particularly preferably 0.72 dl/g to 0.84 dl/g.

The intrinsic viscosity of the polyester film is preferably the lower limit value described above or less from the viewpoint of improving film formation properties and the film thickness uniformity.

<Production Method of Polyester Film>

(Film Forming Step)

In the film forming step, the melt obtained by meting the polyester and the cyclic carbodiimide compound included in the resin composition for forming the polyester film of the present invention is passed through a gear pump or a filter, then extruded from a cooling roll through a die, and cooled and solidified, whereby a (unstretched) film can be formed. In this regard, the extruded melt can be adhered to the cooling roll using an electrostatic application method. At this time, the surface temperature of the cooling roll can be usually set to 10° C. to 40° C.

(Stretching Step)

The (unstretched) film formed by the film forming step can be realized by carrying out a stretching treatment in the stretching step. In the stretching step, a cooling-solidified (unstretched) film is preferably stretched in one or two directions, and more preferably stretched in two directions. The stretching in two directions (biaxial stretching) is preferably stretching in the length direction (MD: Machine Direction) (which is hereinafter also referred to as "longitudinal stretching") and in the width direction (TD: Transverse Direction) (which may be hereinafter also referred to as a "transverse stretching". The longitudinal stretching and the transverse stretching can be performed once, respectively, or may be performed in plural times, and the longitudinal stretching and the transverse stretching may be performed at the same time.

The stretching treatment is performed, preferably at the glass temperature (Tg)° C. of the film to (Tg+60)° C., and more preferably Tg+3° C. to Tg+40° C., and more preferably at Tg+5° C. to Tg+30° C.

The preferable stretching ratio is 280% to 500%, more preferably 300% to 480%, and even more preferably 320% to 460% in at least one direction. In the case of biaxial stretching, the stretching may be performed equivalently in the longitudinal and the transverse directions, but it is more preferable that the stretching ratio in one direction is larger than that in the other direction, thereby carrying out inequivalent stretching. Any one of the longitudinal direction (MD) and the transverse direction (TD) may be larger than the other. The stretching ratio as mentioned herein is determined using the following formula.

Stretching ratio (%)=100{(Length after stretching)−(Length before stretching)}/(Length before stretching)

The biaxial stretching treatment is a stretching, for example, at the glass transition temperature $(Tg_1)°$ C. of a film to $(Tg_1+60)°$ C. in the length direction once or two or more times, in which the total ratio is 3- to 6-times and the ratio in the width ration at $(Tg_1)°$ C. to (Tg+60)° C. is 3- to 5-times.

The biaxial stretching treatment can be performed by stretching in the length direction, using two or more nip rolls that have a higher peripheral speed at an outlet (longitudinal stretching), and can also performed by gripping both ends of the film with chucks and extending them in the perpendicular direction (the direction perpendicular to the length direction) (transverse stretching).

In the stretching step, before the stretching treatment or after the stretching treatment, and preferably after stretching treatment, the film can be subjected to a heat treatment. By carrying out the heat treatment, fine crystals can be produced, thereby improving the dynamic characteristics or durability. The film can also be subjected to a heat treatment at about 180° C. to 210° C. (more preferably at 185° C. to 210° C.) for 1 second to 60 seconds (more preferably for 2 seconds to 30 seconds).

In the stretching step, the thermal relaxation treatment can be performed after the heat treatment. The thermal relaxation treatment is a treatment for shrinking the film by applying heat to the film for stress relaxation. The thermal relaxation treatment is preferably performed in both directions of the MD direction and the TD direction of the film. For the conditions in the thermal relaxation treatment, the treatment is preferably performed at a temperature lower than the heat treatment temperature, and more preferably at 130° C. to 205° C. Further, for the thermal relaxation treatment, the thermal shrinkage (150° C.) of the film in both of the MD and the TD is preferably 1% to 12%, and more preferably 1% to 10%. However, the thermal shrinkage (150° C.) is determined as follows. The thermal shrinkage can be determined from the following formula, by cutting out a sample having a width of 50 mm at 350 mm in the measurement direction, attaching a target point at an interval of 300 mm near the both ends in the length direction of the sample, fixing one end in an oven adjusted to a temperature of 150° C., leaving the other end to be free for 30 minutes, then measuring the distance between the target points at room temperature, taking this length as L (mm), and using this measured values.

150° C. thermal shrinkage (%)=100×(300−L)/300

In addition, a case where the thermal shrinkage is positive denotes shrinkage, and a case where the thermal shrinkage is negative denotes stretching.

As described above, according to the method described above, a film having excellent hydrolysis resistance can be fabricated. The polyester film of the present invention can be appropriately used not only as a protective sheet (back sheet for a solar cell module) for a solar cell module as described below, but also in other applications.

In addition, the film of the present invention can also be used as a laminate including a coating layer containing at least one functional group selected from COON, OH, $SO_3H$, $NH_2$, and a salt thereof thereon.

[Back Sheet for Solar Cell Module]

The back sheet for a solar cell module of the present invention may include the polyester film of the present invention. If the polyester film of the present invention is used for a back sheet for a solar cell module, a problem in adhesiveness among the layers is reduced, and thus, particularly, adhesiveness among the layers after wet heat aging can be greatly improved.

The back sheet for a solar cell module of the present invention may have the following functional layer applied to the polyester film by coating after uniaxial stretching and/or after biaxial stretching. For the application, known coating techniques such as a roll coating method, a knife edge coating method, a gravure coating method, a curtain coating method, and the like can be used.

In addition, a surface treatment (a flame treatment, a corona treatment, a plasma treatment, an ultraviolet treatment, and the like) may also be performed before such the application. Further, bonding using an adhesive is also preferable.

—Readily Adhesive Layer—

In the polyester film of the present invention, a readily adhesive layer is preferably provided on the side facing the sealing material of the battery-side substrate, in which a photovoltaic cell is sealed with a sealing material in the case of constituting the solar cell module. By providing a readily adhesive layer exhibiting adhesiveness to an adherend (for example, the surface of the battery-side substrate and the sealing material, in which the photovoltaic cell is sealed with a sealing material) including a sealing material (in particular, an ethylene-vinyl acetate copolymer), it is possible to adhere firmly between the back sheet and the sealing material. Specifically, the readily adhesive layer preferably has an adhesion power, in particular with EVA (an ethylene-vinyl acetate copolymer) used as a sealing material, of 10 N/cm or greater, and preferably 20 N/cm or greater.

Further, for the readily adhesive layer, it is required that peeling of the back sheet should not occur during the use of the solar cell module, and thus, it is preferable the readily adhesive layer have high hydrolysis resistance.

(1) Binder

The readily adhesive layer according to the present invention can contain at least one binder.

As the binder, a polyester, a polyurethane, an acrylic resin, a polyolefin, or the like can be used. Among these, from the viewpoint of durability, an acrylic resin and polyolefin are preferable. Further, as the acrylic resin, a composite resin of an acryl and a silicone is also preferable. Preferable examples of the binder include the following compounds.

Examples of the polyolefin include CHEMIPEARL S-120 and CHEMIPEARL S-75N (both manufactured by Mitsui Chemicals, Inc.). Examples of the acrylic resin include JURYMER ET-410 and JURYMER SEK-301 (both manufactured by Nihon Junyaku Co., Ltd.). Furthermore, examples of the composite resin of an acryl and a silicone include CERANATE WSA1060 and CERANATE WSA1070 (both manufactured by DIC Corp.), and H7620, H7630, and H7650 (all manufactured by Asahi Kasei Chemicals Corp.). The amount of the binder is preferably in the range of 0.05 $g/m^2$ to 5 $g/m^2$, and particularly preferably in the range of 0.08 $g/m^2$ to 3 $g/m^2$.

When the amount of the binder is 0.05 $g/m^2$ or greater, a more satisfactory adhesive power is obtained, and when the amount of the binder is 5 $g/m^2$ or less, a better surface shape is obtained.

(2) Fine Particles

The readily adhesive layer in the present invention can contain at least one kind of fine particles. The readily adhesive layer preferably contains the fine particles in an amount of 5% by mass or greater with respect to the total mass of the layer.

Suitable examples of the fine particles include inorganic fine particles of silica, calcium carbonate, magnesium oxide, magnesium carbonate, tin oxide, and the like.

Particularly among these, from the viewpoint that a decrease in the adhesiveness is small when exposed to a high-temperature and high-humidity atmosphere, fine particles of tin oxide and silica are preferable.

The particle diameter of the fine particles is preferably about 10 nm to 700 nm, and more preferably about 20 nm to 300 nm. When fine particles having a particle diameter in the range described above are used, satisfactory high adhesiveness can be obtained. There are no particular limitations on the shape of the fine particles, but fine particles having a spherical shape, an indefinite shape, a needle-like shape, and the like can be used.

The amount of the fine particles to be added in the readily adhesive layer is preferably 5% by mass to 400% by mass, and more preferably 50% by mass to 300% by mass, relative to 100% by mass of the binder in the readily adhesive layer.

When the amount of the fine particles to be added is 5% by mass or greater, the adhesiveness when the readily adhesive layer is exposed to a high-temperature and high-humidity atmosphere is excellent. When the amount to be added is 1000% by mass or less, the surface shape of the readily adhesive layer is better.

(3) Crosslinking Agent

The readily adhesive layer in the present invention can contain at least one crosslinking agent.

Examples of the crosslinking agent include an epoxy-based crosslinking agent, an isocyanate-based crosslinking agent, a melamine-based crosslinking agent, a carbodiimide-based crosslinking agent, an oxazoline-based crosslinking agent, and the like. From the viewpoint of securing the adhesiveness after wet heat aging, among these, an oxazoline-based crosslinking agent is particularly preferable.

Specific examples of the oxazoline-based crosslinking agent include 2-vinyl-2-oxazoline, 2-vinyl-4-methyl-2-oxazoline, 2-vinyl-5-methyl-2-oxazoline, 2-isopropenyl-2-oxazoline, 2-isopropenyl-4-methyl-2-oxazoline, 2-isopropenyl-5-ethyl-2-oxazoline, 2,2'-bis-(2-oxazoline), 2,2'-methylene-bis-(2-oxazoline), 2,2'-ethylene-bis-(2-oxazoline), 2,2'-trimethylene-bis-(2-oxazoline), 2,2'-tetramethylene-bis-(2-oxazoline), 2,2'-hexamethylene-bis-(2-oxazoline), 2,2'-octamethylene-bis-(2-oxazoline), 2,2'-ethylene-bis-(4,4'-dimethyl-2-oxazoline), 2,2'-p-phenylene-bis-(2-oxazoline), 2,2'-m-phenylene-bis-(2-oxazoline), 2,2'-m-phenylene-bis-(4,4'-dimethyl-2-oxazoline), bis-(2-oxazolinylcyclohexane)sulfide, bis-(2-oxazolinylnorbornane)sulfide, and the like.

In addition, (co)polymers of these compounds can also be preferably used.

Furthermore, as a compound having an oxazoline group, EPOCROS K2010E, EPOCROS K2020E, EPOCROS K2030E, EPOCROS WS500, and EPOCROS WS700 (all manufactured by Nippon Shokubai Co., Ltd.), and the like can also be used.

A preferable amount of the crosslinking agent to be added in the readily adhesive layer is preferably 5% by mass to 50% by mass, and more preferably 20% by mass to 40% by mass, relative to 100% by mass of the binder in the readily adhesive layer. When the amount of the crosslinking agent to be added is 5% by mass or greater, a good crosslinking effect is obtained, and a decrease in the strength of the reflective layer or adhesion failure does not easily occur. When the amount of the crosslinking agent to be added is 50% by mass or less, the pot life of the coating liquid can be maintained longer.

(4) Additives

To the readily adhesive layer in the present invention, a known mat agent such as polystyrene, polymethyl methacrylate, silica, and the like; a known surfactant such as an anionic surfactant, a nonionic surfactant, and the like; etc. may also be further added, if desired.

(5) Method for Forming Readily Adhesive Layer

Examples of the method for forming the readily adhesive layer in the present invention include a method of bonding a polymer sheet having high adhesiveness to the polyester film, and a method based on coating. A method based on coating is preferable from the viewpoint of being convenient and capable of forming a highly uniform thin film. As the coating method, for example, a known method of using a gravure coater or a bar coater can be used. The solvent for the coating liquid that is used for coating may be water, or an organic solvent such as toluene and methyl ethyl ketone. The solvents may be used singly or as a mixture of two or more kinds thereof.

In addition, in the case of forming a readily adhesive layer by coating, both of drying of the coating layer in a drying zone after the heat treatment as described above, and a heat treatment is preferably included. Further, a case of forming the colored layer as described later or the other functional layers by coating is also preferable.

(6) Physical Properties of Readily Adhesive Layer

The thickness of the readily adhesive layer in the present invention is not particularly limited, but usually, the thickness is preferably 0.05 μm to 8 μm, and more preferably in the range of 0.1 μm to 5 μm. When the thickness of the readily adhesive layer is 0.05 μm or greater, the high adhesiveness that is needed can be easily obtained, and when the thickness is 8 μm or less, the surface shape can be maintained more satisfactorily.

Furthermore, the readily adhesive layer in the present invention is preferably transparent from the viewpoint that when a colored layer (particularly a reflective layer) is arranged between the readily adhesive layer and the polyester film, the readily adhesive layer does not impair the effect of the colored layer.

—Colored Layer—

The polyester film of the present invention can be provided with a colored layer. The colored layer is a layer arranged to be in contact with the surface of the polyester film or with another layer interposed therebetween, and can be constructed using a pigment or a binder.

A first function of the colored layer is to increase the power generation efficiency of a solar cell module by reflecting a portion of light in the incident light, which is not used in the power generation at the photovoltaic cell and reaches the back sheet, and returning the portion of light to the photovoltaic cell. A second function is to enhance the decorative properties of the external appearance when the solar cell module is viewed from the front surface side. Generally, when a solar cell module is viewed from the front surface side, the back sheet is seen around the photovoltaic cell. Thus, the decorative properties can be increased by providing a colored layer to the back sheet.

(1) Pigment

The colored layer in the present invention can contain at least one pigment. The pigment is preferably included in an amount in the range of 2.5 $g/m^2$ to 8.5 $g/m^2$. A more preferable pigment content is in the range of 4.5 $g/m^2$ to 7.5 $g/m^2$. When the pigment content is 2.5 $g/m^2$ or greater, necessary coloration can be easily obtained, and the light reflectivity or decorative properties can be further improved. When the pigment content is 8.5 $g/m^2$ or less, the surface shape of the colored layer can be maintained more satisfactorily.

Examples of the pigment include inorganic pigments such as titanium oxide, barium sulfate, silicon oxide, aluminum oxide, magnesium oxide, calcium carbonate, kaolin, talc, ultramarine blue, Prussian blue, carbon black, and the like; and organic pigments such as phthalocyanine blue, phthalocyanine green, and the like. Among these pigments, a white pigment is preferable from the viewpoint of constituting the colored layer as a reflective layer that reflects sunlight incident thereon. Preferable examples of the white pigment include titanium oxide, barium sulfate, silicon oxide, aluminum oxide, magnesium oxide, calcium carbonate, kaolin, talc, and the like.

The average particle diameter of the pigment is preferably 0.03 μm to 0.8 μm, and more preferably about 0.15 μm to 0.5 μm. When the average particle diameter is in the range described above, the light reflection efficiency may be lowered.

In the case of constructing the colored layer as a reflective layer that reflects sunlight that has entered, the preferable amount of the pigment to be added in the reflective layer varies with the type or average particle diameter of the pigment used and cannot be defined briefly. However, the amount of the pigment to be added is preferably 1.5 $g/m^2$ to 15 $g/m^2$, and more preferably about 3 $g/m^2$ to 10 $g/m^2$. When the addition amount thereof is 1.5 $g/m^2$ or greater, a necessary reflectance can be easily obtained, and when the addition amount thereof is 15 $g/m^2$ or less, the strength of the reflective layer can be maintained at a higher level.

(2) Binder

The colored layer in the present invention can contain at least one binder. When the colored layer contains a binder, the amount of the binder is preferably in the range of 15% by mass to 200% by mass, and more preferably in the range of 17% by mass to 100% by mass, relative to 100% by mass of the pigment. When the amount of the binder is 15% by mass or greater, the strength of the colored layer can be maintained more satisfactorily, and when the amount is 200% by mass or less, the reflectance or decorative properties is lowered.

As the binder suitable for the colored layer, a polyester, a polyurethane, an acrylic resin, a polyolefin, or the like can be used. The binder is preferably an acrylic resin or a polyolefin from the viewpoint of durability. As an acrylic resin, a composite resin of an acryl and a silicone is also preferable. Preferable examples of the binder include the following compounds.

Examples of the polyolefin include CHEMIPEARL S-120 and CHEMIPEARL S-75N (both manufactured by Mitsui Chemicals, Inc.), and the like. Examples of the acrylic resin include JURYMER ET-410 and JURYMER SEK-301 (both manufactured by Nihon Junyaku Co., Ltd.), and the like. Furthermore, examples of the composite resin of an acryl and a silicone include CERANATE WSA1060 and CERANATE WSA1070 (both manufactured by DIC Corp.), H7620, H7630, and H7650 (all manufactured by Asahi Kasei Chemicals Corp.), and the like.

(3) Additives

To the colored layer in the present invention, a crosslinking agent, a surfactant, a filler, or the like may also be further added, if desired, in addition to the binder and the pigment.

Examples of the crosslinking agent include an epoxy-based crosslinking agent, an isocyanate-based crosslinking agent, a melamine-based crosslinking agent, a carbodiimide-based crosslinking agent, an oxazoline-based crosslinking agent, and the like. The amount of the crosslinking agent to be added in the colored layer is preferably 5% by mass to 50% by mass, and more preferably 10% by mass to 40% by mass, relative to 100% by mass of the binder in the colored layer. When the amount of the crosslinking agent to be added is 5% by mass or greater, a good crosslinking effect is obtained, and the strength or adhesiveness of the colored layer can be maintained at a high level. When the amount of the crosslinking agent to be added is 50% by mass or less, the pot life of the coating liquid can be maintained longer.

As the surfactant, a known surfactant such as an anionic surfactant, a nonionic surfactant, and the like can be used. The amount of the surfactant to be added is preferably 0.1 $mg/m^2$ to 15 $mg/m^2$, and more preferably 0.5 $mg/m^2$ to 5 $mg/m^2$. When the amount of the surfactant to be added is 0.1 $mg/m^2$ or greater, generation of cissing can be effectively suppressed, and when the addition amount thereof is 15 $mg/m^2$ or less, excellent adhesiveness is obtained.

Furthermore, the colored layer may also contain a filler such as silica and the like, in addition to the pigments described above. The amount of the filler to be added is preferably 20% by mass or less, and more preferably 15% by mass or less, relative to 100% by mass of the binder in the colored layer. When the colored layer contains a filler, the strength of the colored layer can be increased. Furthermore, when the amount of the filler to be added is 20% by mass or less, the proportion of the pigment can be retained, and therefore, satisfactory light reflectivity (reflectance) or decorative properties are obtained.

(4) Method for Forming Colored Layer

Examples of the method for forming the colored layer include a method of bonding a polymer sheet containing a pigment on the polyester film, a method of co-extruding the colored layer during the molding of the polyester film, and a method based on coating. Among these, the method by coating is preferable from the viewpoint of being convenient and capable of forming a highly uniform thin film. As the coating method, for example, a known method of using a gravure coater or a bar coater can be used. The solvent for the coating liquid used in the coating may be water, or may be an organic solvent such as toluene, methyl ethyl ketone, and the like. However, from the viewpoint of environmental burden, it is preferable to use water as the solvent.

The solvents may be used singly or as a mixture of two or more kinds thereof.

(5) Physical Properties of Colored Layer

It is preferable that the colored layer contain a white pigment and is constructed as a white layer (light reflective layer). In the case where the colored layer is a reflective layer, the light reflectance for light at 550 nm is preferably 75% or greater. When the reflectance is 75% or greater, the portion of sunlight that passes through the photovoltaic cell and is not used in power generation can be returned to the cell, and a large effect of increasing the power generation efficiency is obtained.

The thickness of the white layer (light reflective layer) is preferably 1 µm to 20 µm, more preferably 1 µm to 10 µm, and even more preferably about 1.5 µm to 10 µm. When the thickness is 1 µm or greater, necessary decorative properties or a reflectance can be easily obtained, and when the thickness is 20 µm or less, the surface shape may be deteriorated in some cases.

—Undercoat Layer—

The polyester film in the present invention can be provided with an undercoat layer. For example, when a colored layer is provided, the undercoat layer may be provided between the colored layer and the polyester film. The undercoat layer can be constructed by using a binder, a crosslinking agent, a surfactant, or the like.

Examples of the binder contained in the undercoat layer include polyester, polyurethane, an acrylic resin, a polyolefin, and the like. To the undercoat layer, crosslinking agents such as an epoxy-based crosslinking agent, an isocyanate-based crosslinking agent, a melamine-based crosslinking agent, a carbodiimide-based crosslinking agent, an oxazoline-based crosslinking agent, and the like; surfactants such as an anionic surfactant, a nonionic surfactant, and the like; a filler such as silica and the like; etc. may be added, in addition to the binder.

There are no particular limitations on the method for coating and forming the undercoat layer, or the solvent for the coating liquid used in the method.

As the coating method, for example, a gravure coater or a bar coater can be used. The solvent may be water, or may be an organic solvent such as toluene, methyl ethyl ketone, and the like. The solvents may be used singly or as a mixture of two or more kinds thereof.

Coating may be performed such that the undercoat layer may be applied on a polyester film obtained after biaxial stretching, or may be applied on a polyester film obtained after uniaxial stretching. In this case, the polyester film may be further stretched, after applying the undercoat layer, in the direction different from the direction of initial stretching. Furthermore, the undercoat layer may be applied on a polyester film prior to stretching, and then the polyester film may be stretched in two directions.

The thickness of the undercoat layer is preferably 0.05 µm to 2 µm, and more preferably in the range of about 0.1 µm to 1.5 µm. When the film thickness of the layer is 0.05 µm or greater, necessary adhesiveness can be easily obtained, and when the thickness is 2 µm or less, the surface shape can be maintained satisfactorily.

—Antifouling Layer (Fluorine-Based Resin Layer and Silicon-Based Resin Layer)—

The polyester film of the present invention is preferably provided with at least one of a fluorine-based resin layer and a silicon-based (Si-based) resin layer as an antifouling layer. When a fluorine-based resin layer or a Si-based resin layer is provided, prevention of contamination of the polyester surface and an enhancement of weather resistance can be promoted. Specifically, it is preferable that the polyester film have a fluorine resin-based coating layer such as those described in JP-A-2007-35694 and JP-A-2008-28294, and WO 2007/063698.

Furthermore, it is also preferable that a fluorine-based resin film such as TEDLAR (manufactured by DuPont Company) be adhered to the polyester film.

The thicknesses of the fluorine-based resin layer and the Si-based resin layer are respectively preferably in the range of 1 µm to 50 µm, more preferably in the range of 1 µm to 40 µm, and even more preferably 1 µm to 10 µm.

[Solar Cell Module]

The solar cell module of the present invention may include the polyester film or the back sheet for a solar cell module of the present invention.

The solar cell module of the present invention is constituted such that a photovoltaic cell that converts the light energy of sunlight to electrical energy be arranged between a transparent substrate, on which sunlight is incident, and the polyester film (back sheet for a solar cell) of the present invention. The space between the substrate and the polyester film can be configured to be sealed with a resin (a so-called sealing material) such as an ethylene-vinyl acetate copolymer and the like.

The details of the solar cell module, the photovoltaic cell, and the members other than the back sheet are described in, for example, "Constituent Materials for Photovoltaic Power Generation System" (edited by Eiichi Sugimoto, Kogyo Chosakai Publishing Co., Ltd. published in 2008).

The transparent substrate may desirably have light transmitting properties by which sunlight can be transmitted, and can be appropriately selected from base materials that transmit light. From the viewpoint of power generation efficiency, a base material having higher light transmittance is preferable, and as such a substrate, for example, a glass substrate, a substrate of a transparent resin such as an acrylic resin and the like, etc. can be suitably used.

As the photovoltaic cell, various known photovoltaic cells such as silicon-based elements such as single crystal silicon, polycrystalline silicon, amorphous silicon, and the like; Group III-V or Group II-VI compound semiconductor-based elements such as copper-indium-gallium-selenium, copper-indium-selenium, cadmium-tellurium, gallium-arsenic, and the like; etc. may be applied.

EXAMPLES

Hereinafter, the present invention will be described in more detail with reference to the following Examples. In Examples as described below, the material, the amounts and ratios thereof, the details of the treatment, the treatment procedure, and the like may be suitably modified within a range not departing from the spirit of the present invention.

Therefore, the range of the present invention should not be construed to be limited by the Examples as described below. Unless otherwise specifically indicated, the "part(s)" is on the basis of mass.

As a carbodiimide-based terminal blocking agent, the following compounds were used in each Comparative Example. Moreover, cyclic carbodiimide (1) used in Comparative Example was a compound having the molecular weight of 252 described in Example of JP-A-2011-258641, and was synthesized with reference to the synthesis method described in Reference Example 1 of JP-A-2011-258641.

Cyclic carbodiimide (2) used in Comparative Example was a compound having the molecular weight of 516 described in Example of JP-A-2011-258641, and was synthesized with reference to the synthesis method described in Reference Example 2 of JP-A-2011-258641.

Cyclic carbodiimides (3) to (5) used in Comparative Example was a compound described in WO2010/071211, and was synthesized with reference to the synthesis method described in JWO2010/071211.

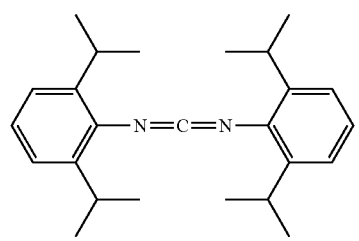

Monocarbodiimide
Stabaxol I (manufactured by Rhein Chemie Rheinau GmbH)
Mw362

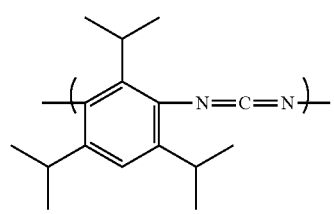

Polycarbodiimide
Stabaxol P400 (manufactured by Rhein Chemie Rheinau GmbH)
Mw 26000

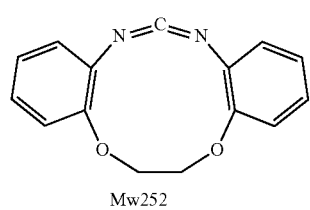

Cyclic carbodiimide (1)
Mw252

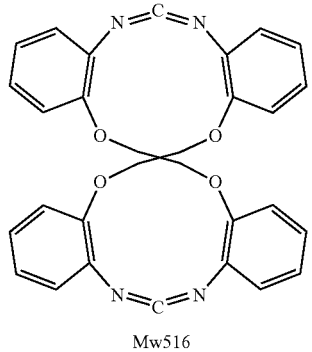

Cyclic carbodiimide (2)
Mw516

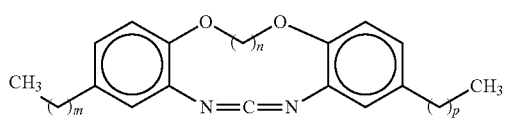

Cyclic carbodiimide (3): (m, p, n = 1, 1, 2)

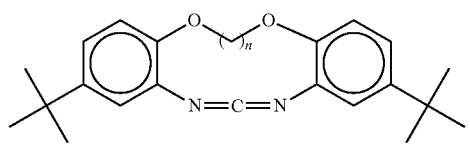

Cyclic carbodiimide (4): (n = 2)

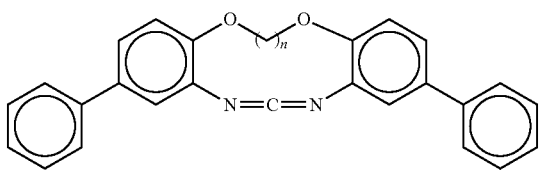

Cyclic carbodiimide (5): (n = 2)

The cyclic carbodiimide compounds which are represented by Formula (O-1) or (O-2) of the present invention having the following structures were used in each Example as the terminal blocking agent.

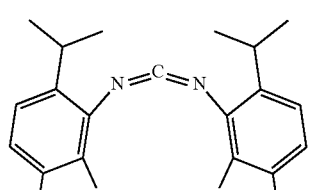

Compound 1
MW336

Compound 2

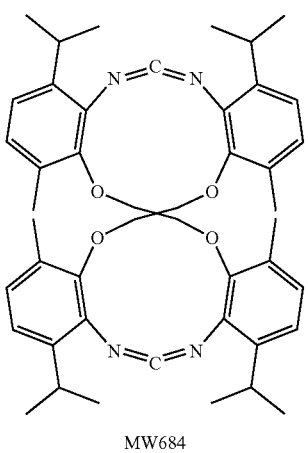

MW684

Compound 3

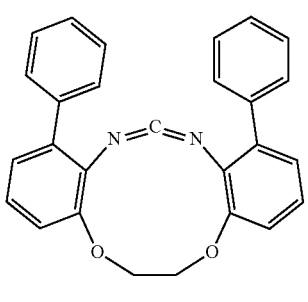

MW404

Compound 4

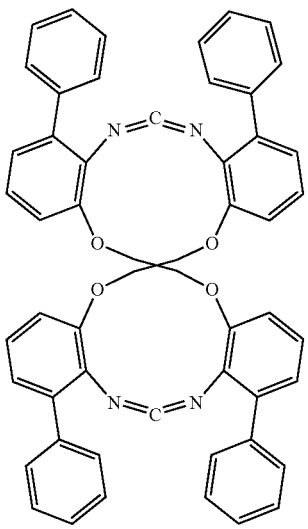

MW821

Compound 5

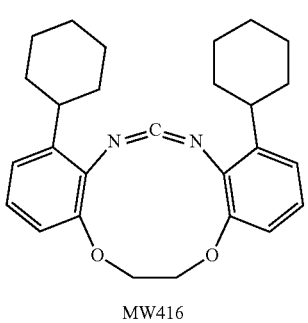

MW416

Compound 6

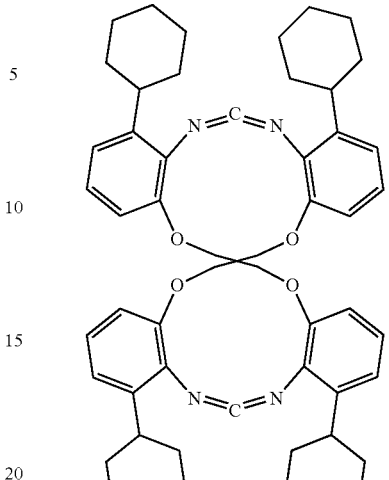

MW845

Among the carbodiimide-based terminal blocking agents described above, a compound used in each Example was synthesized by the following method.

Synthesis Example 1

(Synthesis of Compound 1)

Carvacrol (1.0 mol) and acetic acid (1.6 L) were put into the reactor equipped with a stirrer, a mixed solution of nitric acid (1.1 mol) and 800 ml of acetic acid was slowly added dropwise while stirring, extraction was performed two times on the resultant product with ethyl acetate of 1 L, and the extracted product was sufficiently washed with water. The obtained organic layer was dehydrated using magnesium sulfate and concentrated. Thereafter, the concentrated product was purified by column chromatography, whereby 50 g of ortho-nitro material of carvacrol was obtained.

Then, the obtained nitro material (0.1 mol), 1,2-dibromoethane (0.05 mol), potassium carbonate (0.3 mol), and 200 ml of N,N-dimethylformamide were put into a reactor provided with a stirrer and heater in $N_2$ atmosphere, the mixture was reacted at 130° C. for 12 hours, and DMF was removed by reducing pressure. The obtained solid material was dissolved in 200 ml of dichloromethane and liquid-liquid separation was performed with 100 ml of water three times. The organic layer was dehydrated with 5 g of magnesium sulfate, and dichloromethane was removed by reducing pressure, whereby an intermediate product A (nitro material) was obtained.

Then, the intermediate product A (0.1 mol), 5% palladium on carbon (Pd/C) (1 g), and 200 ml of ethanol/dichloromethane (70/30) were put into a reactor provided with a stirrer, hydrogen substitution was performed five times, the reaction was performed in a state in which hydrogen was supplied at 25° C. all times, and the reaction was ended when the hydrogen reduction no longer occurs. The Pd/C was retrieved, and the mixed solvent was removed, whereby an intermediate product B (amine material) was obtained.

Then, the intermediate product B (0.025 mol), imidazole (0.2 mol), carbon disulfide (0.2 mol), and 150 ml of acetonitrile were put into a reactor provided with a stirrer and a heater in $N_2$ atmosphere. The temperature of the reaction solution was set to 80° C., and the reaction was performed for 15 hours. After the obtained acetonitrile solution was concentrated, the concentrated product was purified by column chromatography, whereby an intermediate product C (thiourea material) was obtained.

Then, the intermediate product C (0.025 mol), 30% NaOH (0.052 mol), benzyltriethylammonium chloride (0.0019 mol), 170 ml of chloroform, and 5.8 ml of methanol were put into a reactor provided with a stirrer and the mixture was stirred. After 10.5% aqueous solution of hypochlorite (0.103 mol) was slowly added dropwise thereto and stirred for 1 hour, a liquid-liquid separation was performed three times with pure water.

The obtained chloroform solution was dehydrated with magnesium sulfate and concentrated, and the concentrated product was washed with hexane two times, whereby an intended compound was obtained. The structure was confirmed by NMR and IR.

$^1$H-NMR (CDCl$_3$) δ (ppm); 1.22 (12H), 2.33 (6H), 3.41 (2H), 4.18 (4H), 6.94 (4H)

By the above reaction, a compound 1 was synthesized.

Synthesis Example 2

(Synthesis of Compound 2)

The nitro material (0.1 mol) obtained in Synthesis Example 1, pentaerythritol tetrabromide (0.025 mol), potassium carbonate (0.3 mol), and 200 ml of N,N-dimethylformamide were put into a reactor provided with a stirrer and heater in N$_2$ atmosphere, the mixture was reacted at 130° C. for 30 hours, and DMF was removed by reducing pressure. The obtained solid material was washed with water, ethanol, and hexane, whereby an intermediate product A (nitro material) was obtained.

Then, the intermediate product A (0.02 mol), 560 ml of 2-isopropanol, and 110 ml of 35% aqueous solution of hydrochloric acid were put into a reactor provided with a stirrer, then, zinc powder (0.8 mol) was slowly added thereto, and reflux was performed for one hour. After the zinc powder was retrieved by filtration, 1.0 L of chloroform was added thereto, and a liquid-liquid separation was performed two times with pure water. The organic layer was dehydrated with magnesium sulfate, and chloroform was removed by reducing pressure, whereby an intermediate product B (amine material) was obtained.

Then, the intermediate product B (0.015 mol), imidazole (0.03 mol), carbon disulfide (0.09 mol), and 50 ml of acetonitrile were put into a reactor provided with a stirrer and a heater in N$_2$ atmosphere. The temperature of the reaction solution was set to 100° C., and the reaction was performed for 15 hours. The solid precipitated after the reaction was retrieved by filtration, and the resultant product was washed with acetonitrile, whereby an intermediate product C (thiourea material) was obtained.

Then, the intermediate product C (0.01 mol), 30% NaOH (0.04 mol), benzyltriethylammonium chloride (0.002 mol), 200 ml of chloroform, and 6.6 ml of methanol were put into a reactor provided with a stirrer and a heater and the mixture was stirred. After 10.5% aqueous solution of hypochlorite (0.08 mol) was slowly added dropwise thereto and stirred for 1 hour, a liquid-liquid separation was performed three times with pure water.

The obtained chloroform solution was dehydrated with magnesium sulfate and concentrated, and the concentrated product was washed with hexane two times, whereby an intended compound was obtained. The structure was confirmed by NMR and IR.

$^1$H-NMR (CDCl$_3$) δ (ppm); 1.22 (24H), 2.20 (12H), 3.42 (4H), 4.42 (8H), 6.94 (8H)

By the above reaction, a compound 2 was synthesized.

Synthesis Example 3

(Synthesis of Compound 3)

171 g of 3-hydroxybiphenyl (1.0 mol) was dissolved in 1700 ml of nitromethane, and after cooling to 2° C. in an ice bath, 34 ml of fuming nitric acid was added dropwise thereto while stirring, and the resultant product was stirred for 12 hours as it is. After adding 200 ml of water thereto, extraction was performed on the reaction product with 500 ml of chloroform, then, the resultant product was washed with 200 ml of hydrochloric acid water and 100 ml of water, and concentrated. Thereafter, the concentrated product was produced by column chromatography, whereby 41 g of 2-nitro-3-hydroxybiphenyl (0.3 mol) was obtained.

Then, the obtained nitro material (0.1 mol), 1,2-dibromoethane (0.05 mol), potassium carbonate (0.3 mol), and 200 ml of N,N-dimethylformamide were put into a reactor provided with a stirrer and heater in N$^2$ atmosphere, the mixture was reacted at 130° C. for 12 hours, and DMF was removed by reducing pressure. The obtained solid material was dissolved in 200 ml of dichloromethane and liquid-liquid separation was performed with 100 ml of water three times. The organic layer was dehydrated with 5 g of magnesium sulfate, and dichloromethane was removed by reducing pressure, whereby an intermediate product A (nitro material) was obtained.

Then, the intermediate product A (0.1 mol), 5% palladium on carbon (Pd/C) (1 g), and 200 ml of ethanol/dichloromethane (70/30) were put into a reactor provided with a stirrer, hydrogen substitution was performed five times, the reaction was performed in a state in which hydrogen was supplied at 25° C. all times, and the reaction was ended when the hydrogen reduction no longer occurs. The Pd/C was retrieved, and the mixed solvent was removed, whereby an intermediate product B (amine material) was obtained.

Then, the intermediate product B (0.025 mol), imidazole (0.2 mol), carbon disulfide (0.2 mol), and 150 ml of acetonitrile were put into a reactor provided with a stirrer and a heater in N$_2$ atmosphere. The temperature of the reaction solution was set to 80° C., and the reaction was performed for 15 hours. After the obtained acetonitrile solution was concentrated, the concentrated product was purified by column chromatography, whereby an intermediate product C (thiourea material) was obtained.

Then, the intermediate product C (0.01 mol), 30% NaOH (0.04 mol), benzyltriethylammonium chloride (0.002 mol), 200 ml of chloroform, and 6.6 ml of methanol were put into a reactor provided with a stirrer and the mixture was stirred. After 10.5% aqueous solution of hypochlorite (0.08 mol) was slowly added dropwise thereto and stirred for 1 hour, a liquid-liquid separation was performed three times with pure water.

The obtained chloroform solution was dehydrated with magnesium sulfate and concentrated, and the concentrated product was washed with hexane two times, whereby an intended compound was obtained. The structure was confirmed by NMR and IR. By the above reaction, a compound 3 was synthesized.

Synthesis Example 4

(Synthesis of Compound 4)

The nitro material (0.1 mol) obtained in Synthesis Example 3, pentaerythritol tetrabromide (0.025 mol), potassium carbonate (0.3 mol), and 200 ml of N,N-dimethylformamide were put into a reactor provided with a stirrer and heater in $N_2$ atmosphere, the mixture was reacted at 130° C. for 12 hours, and DMF was removed by reducing pressure. The obtained solid material was dissolved in 200 ml of dichloromethane and liquid-liquid separation was performed with 100 ml of water three times. The organic layer was dehydrated with 5 g of magnesium sulfate, and dichloromethane was removed by reducing pressure, whereby an intermediate product A (nitro material) was obtained.

Then, the intermediate product A (0.02 mol), 5% palladium on carbon (Pd/C) (1 g), and 200 ml of ethanol/dichloromethane (70/30) were put into a reactor provided with a stirrer, hydrogen substitution was performed five times, the reaction was performed in a state in which hydrogen was supplied at 25° C. all times, and the reaction was ended when the hydrogen reduction no longer occurs. The Pd/C was retrieved, and the mixed solvent was removed, whereby an intermediate product B (amine material) was obtained.

Then, the intermediate product B (0.015 mol), imidazole (0.2 mol), carbon disulfide (0.2 mol), and 150 ml of acetonitrile were put into a reactor provided with a stirrer and a heater in $N_2$ atmosphere. The temperature of the reaction solution was set to 100° C., and the reaction was performed for 15 hours. The solid precipitated after the reaction was retrieved by filtration, and the resultant product was washed, whereby an intermediate product C (thiourea material) was obtained.

Then, the intermediate product C (0.01 mol), 30% NaOH (0.04 mol), benzyltriethylammonium chloride (0.002 mol), 200 ml of chloroform, and 6.6 ml of methanol were put into a reactor provided with a stirrer and a heater and the mixture was stirred. After 10.5% aqueous solution of hypochlorite (0.08 mol) was slowly added dropwise thereto and stirred for 1 hour, a liquid-liquid separation was performed three times with pure water.

The obtained chloroform solution was dehydrated with magnesium sulfate and concentrated, and the concentrated product was washed with hexane two times, whereby an intended compound was obtained. The structure was confirmed by NMR and IR. By the above reaction, a compound 4 was synthesized.

Example 1

1. Preparation of Saturated Polyester Resin
—Step (A)—
4.7 tons of high-purity terephthalic acid and 1.8 tons of ethylene glycol were mixed over 90 minutes to form slurry, and the slurry was continuously supplied to a first esterification reaction tank at a flow rate of 3800 kg/h. Subsequently, an ethylene glycol solution of a citric acid chelated titanium complex (VERTEC AC-420, manufactured by Johnson Matthey Plc.) having Ti metal coordinated with citric acid was continuously supplied, to a first esterification reaction tank and a reaction was performed at a temperature inside the reaction tank of 250° C. and for an average retention time of about 4.4 hours with stirring, thereby obtaining an oligomer. At this time, the citric acid chelated titanium complex was continuously added such that the addition amount of Ti was 9 ppm in terms of elements. At this time, the acid value of the oligomer thus obtained was 500 eq/ton.

The obtained oligomer was transferred to a second esterification reaction tank, and with stirring, the reaction product was allowed to react at a temperature inside the reaction tank of 250° C. for an average retention time of 1.2 hours to obtain an oligomer having an acid value of 180 eq/ton. The inside of the second esterification reaction tank was divided into three zones ranging a first zone to a third zone. At a second zone, an ethylene glycol solution of magnesium acetate was continuously supplied in a manner that the addition amount of Mg was 75 ppm in terms of elements. After that, at a third zone, an ethylene glycol solution of trimethyl phosphate was continuously supplied in a manner that the addition amount of P was 65 ppm in terms of elements. Further, the ethylene glycol solution of trimethyl phosphate was prepared by adding a trimethyl phosphate solution at 25° C. to an ethylene glycol solution at 25° C., followed by stirring at 25° C. for 2 hours (content of phosphorous compounds in the solution: 3.8% by mass).

Thus, an esterification reaction product was obtained.
—Step (B)—
The esterification reaction product obtained in the step (A) was continuously supplied to a first polycondensation reaction tank. Subsequently, polycondensation (transesterification reaction) was performed with stirring the esterification reaction product at a reaction temperature of 270° C. and a pressure inside the reaction tank of 20 torr ($2.67 \times 10^{-3}$ MPa) for an average retention time of about 1.8 hours.

Then, the obtained reaction product was transferred from the first polycondensation reaction tank to a second polycondensation reaction tank, and in this reaction tank, a reaction (transesterification reaction) was performed with stirring under the conditions of a temperature inside the reaction tank of 276° C. and a pressure inside the reaction tank of 5 torr ($6.67 \times 10^{-4}$ MPa) for a retention time of about 1.2 hours.

Subsequently, the reaction product obtained by the transesterification reaction was transferred from the second polycondensation reaction tank to a third polycondensation reaction tank, and in this reaction tank, a reaction (transesterification reaction) was performed with stirring under the conditions of a temperature inside the reaction tank of 276° C. and a pressure inside the reaction tank of 1.5 torr ($2.0`10^{-4}$ MPa) for a retention time of 1.5 hours to obtain a reaction product (polyethylene terephthalate (PET)) having a carboxylic acid value of 22 eq/ton and an IV (intrinsic viscosity) of 0.65 dl/g.

Furthermore, the obtained PET was subjected to a heat treatment (solid-phase polymerization) for 24 hours at 205° C. under a reduced pressure of 50 Pa using a rotary vacuum polymerizer. Moreover, by increasing the solid-phase polymerization time, IV is easily increased and AV is easily reduced, and by increasing the solid-phase polymerization temperature, the AV is easily increased and the IV is easily reduced.

Thereafter, nitrogen gas of 25° C. is flowed into the vacuum polymerizer, and a pellet was cooled to 25° C., whereby PET having a carboxylic acid value of 15 eq/ton and an IV of 0.78 dl/g was obtained.

2. Fabrication of Polyester Film and Evaluation
—Extrusion-Molding (Synthesis Step/Film Forming Step)—
The obtained PET was put into a hopper of double-screw kneading extruder having a diameter 50 mm using a main feeder, and the compound 1 of the present invention was put into a subfeeder, and melting and extrusion were performed at 280° C. The extruded melt was passed through a gear pump and a filter (pore diameter of 20 μm), and extruded from a die to a cooling roll at 20° C., whereby an amorphous sheet was obtained. Moreover, the extruded melt was adhered to the cooling roll using an electrostatic application method.

—Stretching (Biaxial Stretching Step)—

An unstretched film which was extruded onto the cooling roll and solidified was subjected to sequential biaxial stretching by the following method, whereby a polyester film having a thickness of 175 μm was obtained.

<Stretching Method>

(a) Longitudinal Stretching

The unstretched film is passed through between two pairs of nip rolls having different peripheral speed, and by this, the unstretched film was stretched in the longitudinal direction (transport direction). Moreover, the stretching was performed at a preheating temperature of 90° C., a stretching temperature of 90° C., a stretching ratio of 3.5 times, and a stretching speed of 3,000%/sec.

(b) Transverse Stretching

The longitudinally stretched film was transversely stretched under the following conditions using a tenter.

<Conditions>

Preheating temperature: 100° C.
Stretching temperature: 110° C.
Stretching ratio: 4.2 times
Stretching speed: 70%/sec —Heat Fixing and Thermal Relaxation—

Subsequently, the stretched film after finishing the longitudinal stretching and transverse stretching was heat-fixed under the following conditions. Furthermore, after heat fixing, the tenter width was shorten and thermal relaxation was performed under the following conditions.

<Heat Fixing Conditions>

Heat fixing temperature: 198° C.
Heat fixing time: 2 seconds

<Thermal Relaxation Conditions>

Thermal relaxation temperature: 195° C.
Thermal relaxation ratio: 5%

—Winding—

After the heat fixing and the thermal relaxation, both ends of the polyester film were trimmed by 10 cm. Thereafter, after knurling 10 mm width of both ends, the polyester film was wound up at a tension of 25 kg/m. Moreover, the width was 1.5 m, and the winding length was 2,000 m.

In the above manner, the polyester film of Example 1 was fabricated. The obtained sample film has a good surface state in which there is no pit or wrinkle.

—Process Evaluation—

(Increase in Viscosity)

Sensory evaluation of IV of the film was performed, and the increase in viscosity was evaluated based on the following criteria. The obtained results are shown in Table 1 below.

<Criteria>

B: IV (after extrusion)−IV' (before extrusion)≤1.0 dl/g.
D: 1.0 dl/g<IV (after extrusion)−IV' (before extrusion).

(Gas)

Sensory evaluation of the smoke and the smell generated from a die of a double-screw extruder was performed, and the volatilization was evaluated based on the following criteria. The obtained results are shown in Table 1 below.

<Criteria>

B: There was no occurrence of smoke and smell.
C: There was no occurrence of smoke but there was occurrence of smell.
D: There was occurrence of smoke and smell.

—Performance of Polyester Film—

(Wet Heat Resistance (PCT Test))

Hydrolysis resistance was evaluated by a half-life period of a retention rate of tensile elongation at break. The half-life period of a retention rate of tensile elongation at break was evaluated by subjecting the polyester film obtained in Example 1 to a storage treatment (heat treatment) under the conditions of 120° C. and relative humidity of 100% and measuring the storage time when tensile elongation at break (%) shown by the polyester film after storage becomes 50% of tensile elongation at break (%) shown by the polyester film before storage. The obtained results are shown in Table 1 below.

B: The half-life period of tensile elongation at break was 160 hours or greater

C: The half-life period of tensile elongation at break was 130 hours or greater and less than 60 hours D: The half-life period of tensile elongation at break was less than 130 hours.

It shows that as the half-life period of a retention rate of tensile elongation at break is longer, the hydrolysis resistance of the polyester film is excellent.

That is, in the polyester film of the present invention, the half-life period of tensile elongation at break before and after the storage treatment under the conditions of 120° C. and relative humidity of 100% is preferably 130 hours or greater, and more preferably 160 hours or greater.

(Volatile Component)

For the obtained polyester film, the amount of volatile components in the film based on the following criteria was measured by gas chromatography (trade name P&T-GC/MS, manufactured by JASCO Corporation), and evaluation was performed according to the following criteria. The obtained results are shown in Table 1 below.

<Conditions>

The obtained polyester film was heated at 280° C. for 10 minutes, and generated gas was detected.

<Criteria>

B: A compound derived from carbodiimide was under the detection limit.

C: An isocyanate compound derived from carbodiimide was under the detection limit.

D: An isocyanate compound derived from carbodiimide was detected.

(Film Thickness Uniformity)

The variation in the film thickness of polyester film when film formation was continuously performed for 4 hours was evaluated. The obtained results are shown in Table 1 below.

A: The variation in the film thickness is 5% or less.
B: The variation in the film thickness is greater than 5% and 10% or less.
C: The variation in the film thickness is greater than 10% and 15% or less.
D: The variation in the film thickness is greater than 15%.

3. Fabrication of Back Sheet for Solar Cell Module

A back sheet for a solar cell module was fabricated, using the polyester film fabricated in Example 1.

First, on one surface of the polyester film fabricated in Example 1, the following (i) reflective layer and (ii) readily adhesive layer were applied in this order by coating.

(i) Reflective Layer (Colored Layer)

All the components having the following composition were mixed and subjected to a dispersion treatment for 1 hour with a dyno-mill disperser, thereby preparing a pigment dispersion.

<Formulation of Pigment Dispersion>

| | |
|---|---|
| Titanium dioxide | 39.9 parts |
| (TIPAQUE R-780-2, manufactured by Ishihara Sangyo Kaisha, Ltd., 100% by mass of solid content) | |
| Polyvinyl alcohol | 8.0 parts |
| (PVA-105, manufactured by Kuraray Co., Ltd., 10% of solid content) | |
| Surfactant | 0.5 parts |
| (DEMOL EP, manufactured by Kao Corp., 25% of solid content) | |
| Distilled water | 51.6 parts |

Then, using the obtained pigment dispersion, the components having the following composition were mixed to prepare a coating liquid for forming a reflective layer.

<Formulation of Coating Liquid for Forming Reflective Layer>

| | |
|---|---|
| Pigment dispersion above | 71.4 parts |
| Polyacrylic resin water dispersion | 17.1 parts |
| (binder: JURYMER ET410, manufactured by Nihon Junyaku Co., Ltd., 30% by mass of solid content) | |
| Polyoxyalkylene alkyl ether | 2.7 parts |
| (NAROACTY CL95, manufactured by Sanyo Chemical Industries, Ltd., 1% by mass of solid content) | |
| Oxazoline compound (cross-linking agent) | 1.8 parts |
| (EPOCROS WS-700, manufactured by NIPPON SHOKUBAI Co., Ltd., 25% by mass of solid content) | |
| Distilled water | 7.0 parts |

The coating liquid for forming a reflective layer obtained above was coated on the polyester film of Example 1 by a bar coater, and dried at 180° C. for 1 minute, thereby forming a (i) reflective layer (white layer) having a titanium dioxide coating amount of 6.5 g/m².

(ii) Readily Adhesive Layer

All of the components with the following composition were mixed to prepare a coating liquid for a readily adhesive layer. The coating liquid was coated to a binder coating amount of binder of 0.09 g/m² onto the (i) reflective layer, and then dried at 180° C. for 1 minute to form (ii) a readily adhesive layer.

<Composition of Coating Liquid for Forming Readily Adhesive Layer>

| | |
|---|---|
| Polyolefin resin water dispersion | 5.2 parts |
| (carboxylic-containing binder: CHEMIPEARL S75N, manufactured by Mitsui chemicals, Inc., 24% by mass of solid content) | |
| Polyoxyalkylene alkyl ether | 7.8 parts |
| (NAROACTY CL95, manufactured by Sanyo Chemical Industries, Ltd., 1% by mass of solid content) | |
| Oxazoline compound | 0.8 parts |
| (EPOCROS WS-700, manufactured by NIPPON SHOKUBAI Co., Ltd., 25% by mass of solid content) | |
| Silica fine particle water dispersion | 2.9 parts |
| (AEROSIL OX-50, manufactured by Nippon Aerosil Co., Ltd., 10% by mass of solid content) | |
| Distilled water | 83.3 parts |

Next, on the surface side opposite to the side having (i) reflective layer and (ii) the readily adhesive layer of the polyester film formed thereon, the following (iii) undercoat layer, (iv) barrier layer, and (v) antifouling layer were applied by coating successively from the polyester film side.

(iii) Undercoat Layer

All of the components with the following composition were mixed to prepare a coating liquid for forming an undercoat layer. This coating liquid was coated on the polyester film and dried at 180° C. for one minute to form an undercoat layer (dried coating amount: about 0.1 g/m²).

<Composition of Coating Liquid for Forming Undercoat Layer>

| | |
|---|---|
| Polyester resin | 1.7 parts |
| (VYLONAL MD-1200, manufactured by TOYOBO Co., Ltd., 17% by mass of solid content) | |
| Polyester resin | 3.8 parts |
| (sulfonic acid-containing binder: PESRESIN A-520, manufactured by TAKAMATSU OIL&FAT Co., Ltd., 30% by mass of solid content) | |
| Polyoxyalkylene alkyl ether | 1.5 parts |
| (NAROACTY CL95, manufactured by Sanyo Chemical Industries, Ltd., 1% by mass of solid content) | |
| Carbodiimide compound | 1.3 parts |
| (CARBODILITE V-02-L2, manufactured by Nisshinbo Industries, Inc., 10% by mass of solid content) | |
| Distilled water | 91.7 parts |

(iv) Barrier Layer

Subsequently, on the surface of thus formed undercoat layer, an 800 angstroms thick vacuum deposition film of silicon oxide was formed under the following vacuum deposition conditions. The film served as a barrier layer.

<Vacuum Deposition Conditions>

Reactive gas mixing ratio (unit:slm): hexamethyl disiloxane/oxygen gas/helium=1/10/10

Vacuum degree inside vacuum chamber: $5.0 \times 10^{-6}$ mbar

Vacuum degree inside deposition chamber: $6.0 \times 10^{-2}$ mbar

Electric power supplied to cooling and electrode drums: 20 kW

Film conveying speed: 80 m/minute (v) Antifouling Layer

As shown below, coating liquids for forming a first antifouling layer and a second antifouling layer were prepared. The coating liquid for forming the first antifouling layer and the coating liquid for forming the second antifouling layer were coated in this order on the barrier layer, so that an antifouling layer having a bi-layer structure was applied by coating.

<First Antifouling Layer>

—Preparation of Coating Liquid for Forming First Antifouling Layer—

The components with the following composition were mixed to prepare a coating liquid for forming the first antifouling layer.

<Composition of Coating Liquid>

| | |
|---|---|
| CERANATE WSA1070 (manufactured by DIC Corp.) | 45.9 parts |
| Oxazoline compound (cross-linking agent) | 7.7 parts |
| (EPOCROS WS-700, manufactured by NIPPON SHOKUBAI Co., Ltd., 25% by mass of solid content) | |
| Polyoxyalkylene alkyl ether | 2.0 parts |
| (NAROACTY CL95, manufactured by Sanyo Chemical Industries, Ltd., 1% by mass of solid content) | |
| Pigment dispersion used for the reflective layer | 33.0 parts |
| Distilled water | 11.4 parts |

—Formation of First Antifouling Layer—

The obtained coating liquid was coated on the barrier layer to a binder coating amount of 3.0 g/m², and dried at 180° C. for 1 minute to form the first antifouling layer.

—Preparation of Coating Liquid for Forming Second Antifouling Layer—

The components with the following composition were mixed to prepare a coating liquid for forming the second antifouling layer.

<Composition of Coating Liquid>

| | |
|---|---|
| Obbligato (fluorobinder, manufactured by AGC Coat-tech) | 45.9 parts |
| Oxazoline compound (EPOCROS WS-700, manufactured by NIPPON SHOKUBAI Co., Ltd., 25% by mass of solid content) | 7.7 parts |
| Polyoxyalkylene alkyl ether (NAROACTY CL95, manufactured by Sanyo Chemical Industries, Ltd., 1% by mass of solid content) | 2.0 parts |
| Pigment dispersion used for the reflective layer | 33.0 parts |
| Distilled water | 11.4 parts |

—Formation of Second Antifouling Layer—

The obtained coating liquid for forming the second antifouling layer was coated on the first antifouling layer formed on the barrier layer to a binder coating amount of 2.0 g/m2, and dried at 180° C. for 1 minute to form the second antifouling layer.

As described above, the back sheet for a solar cell module of Example 1, which has a reflective layer and readily adhesive layer on one side of the polyester film, and has an undercoat layer, a barrier layer, and an antifouling layer on the other side, was fabricated.

Examples 2 to 8 and Comparative Examples 1 to 10

In the same manner as in Example 1 except for using the materials described in the following Table 1, a polyester film of each of Examples and Comparative Examples was produced.

In the same manner as in Example 1 except for using the obtained polyester film of each of Examples and Comparative Examples, aback sheet for a solar cell module of each of Examples and Comparative Examples was fabricated.

In each of Examples and Comparative Examples, the results of evaluation performed in the same manner as in Example 1 are shown in Table 1 below.

TABLE 1

| | Carbodiimide | | Production adaptibility | | Polyester film performance | | |
|---|---|---|---|---|---|---|---|
| | Type | Amount [with respect to 100 parts by mass of polyester] | Increase in viscosity | Gas volatilization | Wet heat resistance | Volatile component | Film thickness uniformity |
| Comparative Example 1 | Monocarbodiimide | 0.4 parts by mass | B | D | C | D | B |
| Comparative Example 2 | Polycarbodiimide | 0.4 parts by mass | B | D | C | D | B |
| Comparative Example 3 | Polycarbodiimide | 1.0 parts by mass | B | D | B | D | B |
| Comparative Example 4 | Cyclic carbodiimide (1) | 0.4 parts by mass | D | B | C | B | C |
| Comparative Example 5 | Cyclic carbodiimide (1) | 1.0 parts by mass | D | C | B | C | D |
| Comparative Example 6 | Cyclic carbodiimide (2) | 0.4 parts by mass | D | B | C | B | D |
| Comparative Example 7 | Cyclic carbodiimide (2) | 1.0 parts by mass | D | B | B | B | D |
| Comparative Example 8 | Cyclic carbodiimide (3) | 0.4 parts by mass | D | B | B | B | C |
| Comparative Example 9 | Cyclic carbodiimide (4) | 0.4 parts by mass | D | B | B | B | C |
| Comparative Example 10 | Cyclic carbodiimide (5) | 0.4 parts by mass | D | B | B | B | C |
| Example 1 | Compound 1 of the present invention | 0.4 parts by mass | B | B | B | B | B |
| Example 2 | Compound 1 of the present invention | 1.0 parts by mass | B | B | B | B | B |
| Example 3 | Compound 1 of the present invention | 2.0 parts by mass | B | C | B | C | B |
| Example 4 | Compound 2 of the present invention | 0.4 parts by mass | B | B | B | B | B |
| Example 5 | Compound 2 of the present invention | 1.0 parts by mass | B | B | B | B | B |
| Example 6 | Compound 2 of the present invention | 2.0 parts by mass | B | B | B | B | B |
| Example 7 | Compound 3 of the present invention | 1.0 parts by mass | B | C | B | C | B |
| Example 8 | Compound 4 of the present invention | 1.0 parts by mass | B | B | B | B | B |

From the above Table 1, when using cyclic carbodiimide compounds 1 to 4 which are represented by Formula (O-1) or (O-2) of the present invention used in each Example, it was possible to suppress increase in viscosity during the film production and suppress generation of isocyanate gas, and the obtained polyester film of each Example was excellent in hydrolysis resistance, did not contain isocyanate having a low molecular weight in the film, did not increase viscosity, and was good in the film thickness uniformity.

Moreover, the present invention is not limited to exhibit the following effects, and the polyester film of each Example was also good in wet heat resistance.

In contrast, in the polyester film of Comparative Examples 1 to 3 using monocarbodiimide or polycarbodiimide having a non-cyclic structure, isocyanate was generated during the film production, and a volatile component was included in the film.

In the polyester film of Comparative Example 4 using a small amount of cyclic carbodiimide (1) of a monocycle which does not have a specific functional group at an ortho-position of an arylene group, increase in viscosity was large during the film production, and the film production stability was poor.

In the polyester film of Comparative Example 5 using cyclic carbodiimide (1) of a monocycle which does not have a specific functional group at an ortho-position of an arylene group, increase in viscosity occurred during the film production, and the film thickness uniformity of the film was poor.

In the polyester films of Comparative Examples 6 and 7 using cyclic carbodiimide (2) of a bicycle which does not have a specific functional group at an ortho-position of an arylene group, increase in viscosity occurred large during the film production, and the film thickness uniformity of the film was poor.

In the polyester film of Comparative Example 8 using cyclic carbodiimide (3) of a cycle which has, at a meta-position, a specific functional group at an ortho-position of an arylene group, increase in viscosity was large during the film production, and the film production stability was poor.

In the polyester film of Comparative Example 9 using cyclic carbodiimide (4) of a cycle which has, at a meta-position, a specific functional group at an ortho-position of an arylene group, increase in viscosity was large during the film production, and the film production stability was poor.

In the polyester film of Comparative Example 10 using cyclic carbodiimide (5) of a cycle which has, at a meta-position, a specific functional group at an ortho-position of an arylene group, increase in viscosity was large during the film production, and the film production stability was poor.

[Fabrication of Solar Cell Module]

The back sheet for a solar cell module of each Example fabricated as described above was bonded to a transparent filler to form the structure as in FIG. 1 in JP-A-2009-158952, thereby fabricating a solar cell module.

At this time, adhesion was made such that the readily adhesive layer of the back sheet for a solar cell module of each Example was in contact with the transparent filler in which photovoltaic cells were embedded.

It was confirmed that the fabricated solar cell module can generate power stably over a long period of time.

While the present invention has been described in detail and with reference to specific embodiments thereof, it will be apparent to one skilled in the art that various changes and modifications can be made therein without departing from the spirit and scope thereof.

The present disclosure relates to the subject matter contained in International Application No. PCT/JP2013/062184, filed on Apr. 25, 2013; Japanese Application No. 2012-113227, filed on May 17, 2012; and Japanese Application No. 2012-180258, filed on Aug. 15, 2012, the contents of which are expressly incorporated herein by reference in their entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims set forth below.

What is claimed is:

1. A cyclic carbodiimide compound which is represented by the following Formula (O-1) or (O-2):

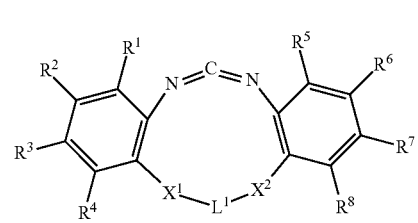

Formula (O-1)

wherein each of $R^1$ and $R^5$ independently represents an alkyl group, an aryl group, or an alkoxy group; each of $R^2$ to $R^4$ and $R^6$ to $R^8$ independently represents a hydrogen atom, an alkyl group, an aryl group, or an alkoxy group; $R^1$ to $R^8$ are not to be bonded to each other to form a ring; each of $X^1$ and $X^2$ independently represents —O—, —CO—, —S—, —SO$_2$—, or —NH—; and $L^1$ represents a divalent aliphatic group having 1 to 20 carbon atoms;

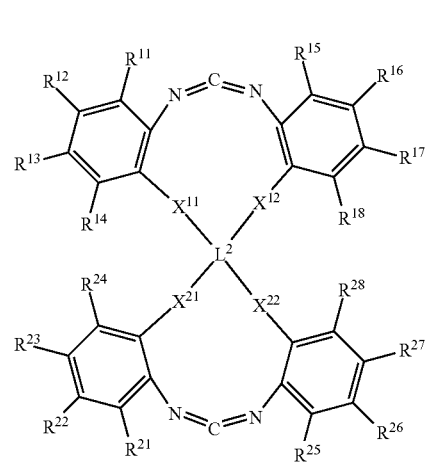

Formula (0-2)

wherein each of $R^{11}$, $R^{15}$, $R^{21}$ and $R^{25}$ independently represents an alkyl group, an aryl group, or an alkoxy group; each of $R^{12}$ to $R^{14}$, $R^{16}$ to $R^{18}$, $R^{22}$ to $R^{24}$, and $R^{26}$ to $R^{28}$ independently represents a hydrogen atom, an alkyl group, an aryl group, or an alkoxy group; $R^{11}$ to $R^{28}$ are not to be bonded to each other to form a ring; each of $X^{11}$, $X^{12}$, $X^{21}$, and $X^{22}$ independently represents —O—, —CO—, —S—, —SO$_2$—, or —NH—; and $L^2$ represents a tetravalent aliphatic group having 1 to 20 carbon atoms.

2. The cyclic carbodiimide compound according to claim 1, wherein both $R^2$ and $R^6$ in Formula (O-1) are hydrogen atoms.

3. The cyclic carbodiimide compound according to claim 1, wherein each of $R^1$, $R^5$, $R^{11}$, $R^{15}$, $R^{21}$ and $R^{25}$ in Formulas (O-1) and (O-2) independently represents a secondary or tertiary alkyl group, or an aryl group.

4. A polyester film, comprising a cyclic carbodiimide compound which is represented by the following Formula (O-1) or (O-2), and a polyester:

Formula (O-1)

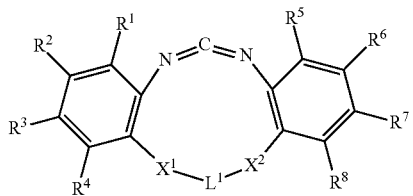

wherein each of $R^1$ and $R^5$ independently represents an alkyl group, an aryl group, or an alkoxy group; each of $R^2$ to $R^4$ and $R^6$ to $R^8$ independently represents a hydrogen atom, an alkyl group, an aryl group, or an alkoxy group; $R^1$ to $R^8$ are not to be bonded to each other to form a ring; each of $X^1$ and $X^2$ independently represents —O—, —CO—, —S—, —SO$_2$—, or —NH—; and $L^1$ represents a divalent aliphatic group having 1 to 20 carbon atoms;

Formula (0-2)

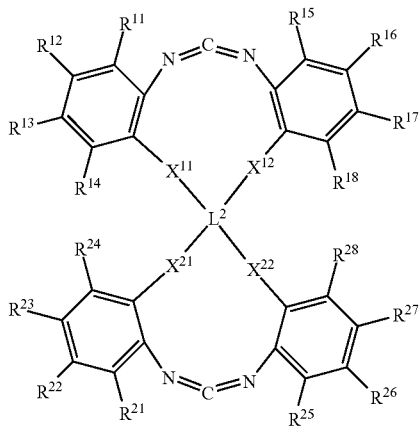

wherein each of $R^{11}$, $R^{15}$, $R^{21}$ and $R^{25}$ independently represents an alkyl group, an aryl group, or an alkoxy group; each of $R^{12}$ to $R^{14}$, $R^{16}$ to $R^{18}$, $R^{22}$ to $R^{24}$, and $R^{26}$ to $R^{28}$ independently represents a hydrogen atom, an alkyl group, an aryl group, or an alkoxy group; $R^{11}$ to $R^{28}$ are not to be bonded to each other to form a ring; each of $X^{11}$, $X^{12}$, $X^{21}$ and $X^{22}$ independently represents —O—, —CO—, —S—, —SO$_2$—, or —NH—; and $L^2$ represents a tetravalent aliphatic group having 1 to 20 carbon atoms.

5. The polyester film according to claim 4, wherein both $R^2$ and $R^6$ in Formula (O-1) are hydrogen atoms.

6. The polyester film according to claim 4, wherein each of $R^1$, $R^5$, $R^{11}$, $R^{15}$, $R^{21}$ and $R^{25}$ in Formulas (O-1) and (O-2) independently represents a secondary or tertiary alkyl group, or an aryl group.

7. The polyester film according to claim 4, comprising the cyclic carbodiimide compound in an amount of 0.05% by mass to 5% by mass relative to 100% by mass of the polyester.

8. The polyester film according to claim 4, wherein a component derived from carboxylic acid in the polyester is a component derived from an aromatic dibasic acid or its derivative for forming an ester.

9. The polyester film according to claim 4 which is biaxially oriented.

10. A solar cell module having a polyester film comprising a cyclic carbodiimide compound which is represented by the following Formula (O-1) or (O-2), and a polyester:

Formula (O-1)

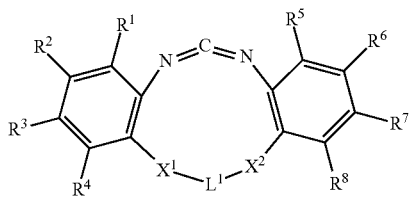

wherein each of $R^1$ and $R^5$ independently represents an alkyl group, an aryl group, or an alkoxy group; each of $R^2$ to $R^4$ and $R^6$ to $R^8$ independently represents a hydrogen atom, an alkyl group, an aryl group, or an alkoxy group; $R^1$ to $R^8$ are not to be bonded to each other to form a ring; each of $X^1$ and $X^2$ independently represents —O—, —CO—, —S—, —SO$_2$—, or —NH—; and $L^1$ represents a divalent aliphatic group having 1 to 20 carbon atoms;

Formula (0-2)

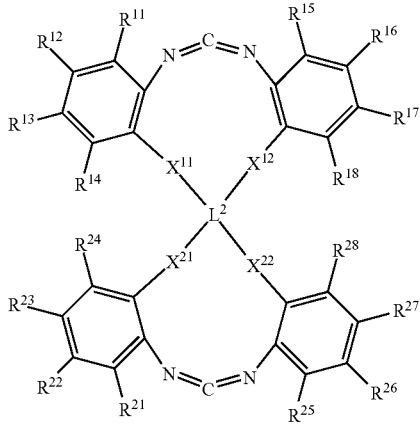

wherein each of $R^{11}$, $R^{15}$, $R^{21}$ and $R^{25}$ independently represents an alkyl group, an aryl group, or an alkoxy group; each of $R^{12}$ to $R^{14}$, $R^{16}$ to $R^{18}$, $R^{22}$ to $R^{24}$, and $R^{26}$ to $R^{28}$ independently represents a hydrogen atom, an alkyl group, an aryl group, or an alkoxy group; $R^{11}$ to $R^{28}$ are not to be bonded to each other to form a ring; each of $X^{11}$, $X^{12}$, $X^{21}$ and $X^{22}$ independently represents —O—, —CO—, —S—, —SO$_2$—, or —NH—; and $L^2$ represents a tetravalent aliphatic group having 1 to 20 carbon atoms.

11. The solar cell module according to claim 10, having the polyester film as a back sheet of the solar cell module.

* * * * *